US008236487B2

(12) United States Patent
Natunen et al.

(10) Patent No.: US 8,236,487 B2
(45) Date of Patent: Aug. 7, 2012

(54) TUMOR SPECIFIC OLIGOSACCHARIDE SEQUENCES AND USE THEREOF

(75) Inventors: Jari Natunen, Helsinki (FI); Susann Teneberg, Hindås (SE); Karl-Anders Karlsson, Göteborg (SE); Tero Satomaa, Helsinki (FI); Annamari Heiskanen, Helsinki (FI)

(73) Assignee: Glykos Finland Oy, Helsinki (FI)

( * ) Notice: Subject to any disclaimer, the term of this patent is extended or adjusted under 35 U.S.C. 154(b) by 1196 days.

(21) Appl. No.: 10/487,203

(22) PCT Filed: Aug. 20, 2002

(86) PCT No.: PCT/FI02/00681
§ 371 (c)(1),
(2), (4) Date: Jun. 2, 2004

(87) PCT Pub. No.: WO03/016915
PCT Pub. Date: Feb. 27, 2003

(65) Prior Publication Data
US 2005/0014718 A1    Jan. 20, 2005

(30) Foreign Application Priority Data
Aug. 20, 2001  (FI) .................................... 20011671

(51) Int. Cl.
*C12Q 1/00* (2006.01)
(52) U.S. Cl. ........................................................... 435/4
(58) Field of Classification Search .................. None
See application file for complete search history.

(56) References Cited

U.S. PATENT DOCUMENTS

| 5,605,807 A | 2/1997 | Dennis |
| 6,391,634 B1 * | 5/2002 | Rook et al. .................... 435/340 |
| 2007/0265170 A1 | 11/2007 | Blixt et al. |

FOREIGN PATENT DOCUMENTS

| DE | 3807594 A1 | 9/1989 |
| EP | 0255342 A1 | 2/1988 |
| WO | WO 8904490 A1 * | 5/1989 |
| WO | WO 0021552 A1 | 4/2000 |
| WO | WO 02056893 A1 | 7/2002 |
| WO | WO-2006/068758 A2 | 6/2006 |

OTHER PUBLICATIONS

Kastrub et al. (Tissue Antigens 2000; 56: 129-135).*
Iyer et al. (Arch. BioChem Biophys. 177, 330-3.*
Kyselova et al. (2008) Clinical Chemistry 54:1166-1175).*
Kyselova et al. (2007) J. Proteome Res 6:1822-1832).*
Iyer et al. (Arch. BioChem Biophys. 177, 330-3).*
Knight (BioTechnology vol. 7 No. 1, Jan. 1989).*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Misonou et al (J. Proteome Research, 2009, 2990-3005).*
European Journal of Biochemistry, Tamao Endo et al, vol. 236, 1996, pp. 579-590.
British Journal of Cancer, PJ Johnson et al, vol. 83, No. 10, 2000, pp. 1330-1337.
European Journal of Biochemistry, Dennis et al, vol. 161, 1986, pp. 359-373.
Histochemical Journal, Chechik et al, vol. 24, 1992, pp. 15-30.
Molecular Immunology, Volman et al, vol. 24, No. 8, 1987, pp. 871-886.
Cancer Research, Hanisch et al, vol. 53, 1993, pp. 4791-4796.
Cancer Research, Meichenin et al, vol. 60, 2000, pp. 5499-5507.
Archives of Biochemistry and Biophysics, Holmes et al, vol. 288, No. 1, 1991, pp. 87-96.
Clinical Cancer Research, Rebbaa et al, vol. 5, 1999, pp. 3661-3668.
Clinical Cancer Research, Cole et al, vol. 3, 1997, pp. 567-873.
Glycobiology, Medina et al, vol. 8, No. 8, 1998, pp. 383-391.
Biochemica et Biophysica Acta, Slawson et al, vol. 1537, 2001, pp. 147-157.
Cancer Research, Yamashita et al, vol. 43, 1983, pp. 5059-5063.
Japanese Journal of Cancer Research, Nakayama et al , vol. 81, 1990, pp. 388-395.
Database WPI Week 199049, Derwent Publications Ltd., London, GB; AN 1990-365935 & JP 22 64864 A (Shinetsu Chem Ind Co. Ltd) Oct. 29, 1990 abstract.
Glycobiology, Hu et al, vol. 4, No. 3, 1994, pp. 251-257.
Patent Abstracts of Japan, vol. 2000, No. 10, Nov. 17, 2000 & JP 20000191685 A (Nippon Koutai Kenkyusho KK), abstract.
Experimental Gerontology, Penno et al, vol. 27, 1992, pp. 493-501.
Roche, N. et al., "Helicobacter pylori and Complex Gangliosides", Infection Immunity, vol. 72, No. 3, pp. 1519-1529, 2004.
Mahdavi, J. et al., "Helicobacter pyloru SabA Adhesin in Persistent Infection and Chronic Inflammation", Science, vol. 297, pp. 573-578, 2002.
Kyselova, Z. et al., "Breast Cancer Diagnosis and Prognosis through Quantitative Measurements of Serum Glycan Profiles", Clinical Chemistry, vol. 54, No. 7, pp. 1166-1175, 2008.
Saldova, R. et al., "Ovarian cancer is associated with changes in glycosylation in both acute-phase proteins and IgG", Glycobiology, vol. 17, No. 12, pp. 1344-1356, 2007.
Ressom, H.W. et al., "Analysis of MALDI-TOF Mass Spectrometry Data for Discovery of Peptide and Glycan Biomarkers of Hepatocellular Carinoma", J. Proteome Res., vol. 7, No. 2, pp. 603-610, 2008.
Kyselova, Z. et al., "Alteration in the Serum Glycome Due to Metastatic Prostate Cancer", J. Proteome Res., vol. 6, pp. 1822-1832, 2007.
Mechref, Y. et al., "Quantitative Serum Glycomics of Esophageal Adenocarcinoma and Other Esophageal Disease Onsets", J. Proteome Res., vol. 8, pp. 2656-2666, 2009.

(Continued)

*Primary Examiner* — Sean Aeder
(74) *Attorney, Agent, or Firm* — Birch, Stewart, Kolasch & Birch, LLP

(57) ABSTRACT

The present invention describes oligosaccharide sequences, which are specifically expressed by human tumors. The present invention is related to a method of determining an oligosaccharide sequence, which comprises a tumor specific terminal N-acetylglucosamine residue, in a biological sample, the presence of said sequence in said sample being an indication of the presence of cancer. The present invention provides antigenic substances comprising said oligosaccharide sequences in a polyvalent form and it further provides diagnostic agents, pharmaceutical compositions and cancer vaccines comprising said oligosaccharide sequences or substances binding to said oligosaccharide sequences. The present invention is also related to methods for the treatment of cancer.

21 Claims, 14 Drawing Sheets

OTHER PUBLICATIONS

Wandall, H.H. et al., "Cancer Biomakers Defined by Autoantibody Signatures to Aberrant O-Glycopeptide Epitopes", Cancer Res., vol. 70, pp. 1306-1313, 2010.

Blixt, O. et al., "Autoantibodies to aberrantly glycosylated MUC1 in early stage breast cancer are associated with a better prognosis", Breast Cancer Research, vol. 13, R25, 2011.

Misonou, Y. et al., "Comprehensive Clinico-Glycomic Study of Colorectal Cancer Specimens: Elucidation of Aberrant Glycosylation and Its Mechanistic Causes in Colorectal Cancer Cells", J. Proteome Res., vol. 8, pp. 2990-3005, 2009.

Satomaa, T. et al., "Analysis of the Human Cancer Glycome Identifies a Novel Group of Tumor-Associated N-Acetylglucosamine Glycan Antigens", Cancer Research, vol. 69, No. 14, pp. 5811-5819, 2009.

Shida, K. et al., "Unusal accumulation of sulfated glycosphingolipids in colon cancer cells", Glycobiology, vol. 19, No. 9, pp. 1018-1033, 2009.

Saarela, S. et al., "The *Escherichida coli* G-Fimbrial Lectin Protein Participates Both in Fimbrial Biogenesis and in Recognition of the Receptor N-Acetyl-$_D$-Glucosamine", Journal of Bacteriology, vol. 177, No. 6, pp. 1477-1484, 1995.

Renkonen, O. et al., "Synthesis of a new nanomolar saccharide inhibitor of lymphocyte adhesion: different polylactosamine backbones present multiple sialyl Lewis x determinants to L-selectin in high-affinity mode", Glycobiology, vol. 7, No. 4, pp. 453-461, 1997.

Toppila, S. et al., "Ezymatic synthesis of α3' sialylated and multiply α3fucosylated biatennary polylactosamines", Eur. j. Biochem., vol. 261, pp. 208-215, 1999.

Teneberg, S. et al., "Molecular mimicry in the recognition of glycosphingolipids by Galα3Galβ4GlcNAcβ-binding *Clostridium difficile* toxin A, human natural anti α-galactosyl IgG and the monoclonal antibody Gal-13: characterizatin of a binding-active human glycosphingolipid, non-identical with the animal receptor", Glycobiology, vol. 6, No. 6, pp. 599-609, 1996.

Ross and Greene, "Targeted therapy in oncology: the agony and ecstasy of personalized medicine", Exp. Rev Anticancer Ther., vol. 1, pp. 321-322, 2001.

Maaheimo, H. et al., "Synthesis of a divalent sialyl Lewis x O-glcan, a potent inhibitor of lymphocyte-endothelium adhesion", Eur. J. Biochem, vol. 234, pp. 616-625, 1995.

Helin, J. et al., Carbohydrate Res., Abstract, vol. 266, No. 2, pp. 191-209, 1995.

Unversagt, Carbohydrate Res. Abstract, vol. 305, pp. 423-431, 1997.

\* cited by examiner

TUMOR SPECIFIC OLIGOSACCHARIDE SEQUENCES AND USE THEREOF

FIELD OF THE INVENTION

The present invention relates to oligosaccharide sequences, which are specifically expressed by human tumors. The present invention describes methods for the detection of the tumor specific oligosaccharide structures of the invention as well as methods for the production of reagents binding to said oligosaccharide sequences. The invention is also directed to the use of said oligosaccharide sequences and reagents binding to them for diagnostics of cancer and malignancies. Furthermore the invention is directed to the use of said oligosaccharide sequences and reagents binding to them for the treatment of tumors, cancers and malignancies.

BACKGROUND OF THE INVENTION

Various tumors express oligosaccharide sequences which are different from the non-malignant glycosylation of the same cell or tissue type. Examples of the known or speculated cancer associated oligosaccharide structures include: glycolipid structures such as globo-H (Fucα2Galβ3GalNAcβ3Galα4LacβCer), gangliosides: GM1 Galβ3GalNAcβ4(NeuNAcα3)LacβCer or GD2 GalNAcβ4(NeuNAcα8NeuNAcα3)LacβCer; Lewis-type fucosylated structures such as Lewis a and x: Galβ3/4(Fucα4/3) GlcNAc, Lewis y: Fucα2Galβ4(Fucα3)GlcNAc, sialyl-Lewis x: NeuNAcα3Galβ4(Fucα3)GlcNAc, and some combinations of these on polylactosamine chains; O-glycan core structures, such as T-antigen Galβ3GalNAcαSer/Thr-Protein, Tn-antigen GalNAcαSer/Thr-Protein or sialyl Tn-antigen NeuNAcα6GalNAcαSer/Thr-Protein. Presence of non-human structures such as N-glycolyl-neuraminic acid in cancers has also been indicated. Association and specificity of oligosaccharide structures with regard to cancers have been well established only in few cases, some of the structures are present in normal cells and tissues and are possibly only more concentrated in cancers.

One report has indicated that structures with terminal GlcNAcβ3Galβ4GlcNAc sequence are present in human leukaemia cells (Hu et al., 1994). The structures may also be equally present on normal leukocytes. Thus, the relation of the finding to glycosylation patterns generally present in solid tumors was not indicated. This type of saccharide structures may be a part of rare normal glycosylations of human tissues: GlcNAcβ3Galβ4GlcNAcβ6 sequence linked on O-glycans is probably present on human gastric mucin. A study shows that a monoclonal antibody recognizing GlcNAcβ3Galβ4GlcNAcβ6 sequence may possibly recognize similar structures on malignant tissues, such as mucinous ovarian neoplasms, pseudopyloric metaplasia of gallbladder and pancreatic epithelia, gastric differentiated carcinoma of stomach, gallbladder and pancreas, and on non-malignant tissues, such as human amniotic fluid, but, however, the structures from malignant tissues were not characterized (Hanisch et al., 1993). The antibody did not recognize neoglycolipid structure GlcNAcβ3Galβ4GlcNAcβ3Galβ4 nor carcinomas of lung, colorectum, endometrium or other organs. Another monoclonal antibody raised against testicular cells probably recognizes branched N-acetyllactosamines such as GlcNAcβ3(GlcNAcβ6)Galβ4GlcNAc- (Symington et al., 1984). Terminal GlcNAc has also been reported from mucins of human foetal mucin (Hounsell et al., 1989). In normal tissues terminal GlcNAc may be present in minor amounts as biosynthetic intermediates in the biosynthesis of poly-N-acetyllactosamines.

Several monoclonal antibodies has been raised against a semisynthetic glycolipid GlcNAcβ3Galβ4GlcNAcβ3LacβCer, these antibodies were shown to recognize glycolipids from cultured colon cancer cell lines and tumors (Holmes et al., 1991). However, the antibodies recognized several structures and the binding data was contradictory. Moreover the glycolipids were not recognized by all of the antibodies and the glycolipid structures from cancer cells or tumors were not characterized. Therefore the presence of terminal GlcNAc structures on tumors were not established. Another study showed production of a monoclonal antibody against GlcNAcβ3LacβCer (Nakamura et al., 1993). This antibody also weakly recognized the pentasaccharide structure described above. Moreover, the antibody recognized a protease sensitive epitope on COS-1 cells, which cell line is not of human origin. The immunization protocols of these studies did not describe induced antibody responses against polyvalent conjugates of the saccharides, but immunization by glycolipids.

Normally there are large amounts of antibodies recognizing terminal GlcNAc structures in human serum. There are also a class of natural antibodies recognizing terminal Galα3Galβ4GlcNAc- structures. The Galα antigen is not naturally present in man and recently it was also shown that the natural antibodies bind structures such as GalNAcα3Galβ4GlcNAc, GalNAcβ3Galβ4GlcNAc, and GlcNAcβ3Galβ4GlcNAc (Teneberg et al., 1996). The X2-structure, GalNAcβ3Galβ4GlcNAc, is a normal antigen on human tissues and structures GalNAcα3Galβ4GlcNAc and Galα3Galβ4GlcNAc have not been described from normal or cancer tissues. Thus, the present finding that the terminal GlcNAc structure is a tumor antigen indicates that the actual function of the natural antibodies might be the prevention of cancers having terminal GlcNAc structures.

The following patents describe cancer antigens and their use for making antibodies for therapeutic and diagnostic uses and for cancer vaccines. The antigen structures are not related to saccharides of the present invention:
Cancer vaccines: U.S. Pat. Nos. 5,102,663; 5,660,834; 5,747,048; 5,229,289 and 6,083,929.
Therapeutic antibodies: U.S. Pat. Nos. 4,851,511; 4,904,596; 5,874,060; 6,025,481 and 5,795,961.
Diagnostics: U.S. Pat. Nos. 4,725,557; 5,059,520; 5,171,667; 5,173,292; 6,090,789; 5,708,163; 5,679,769; 5,543,505; 5,902,725 and 6,203,999.

In the prior art tumor diagnostic and therapeutic antibodies recognizing chitobiose-mannose trisaccharides has been described in DE 38 07 594 A1. The application also describes other N-glycans with numerous varying terminal structures some of which may also comprise non-reducing terminal N-acetyl glucosamine. Several of the desired structures have been later characterized as normal glycans and not cancer specific structures. The application claims to describe structures useful for cancer applications. However, it is not quite clear from the application what the structures of desired glycan are. It is indicated that the GlcNAc residues can be α2, α4, or α6-linked. The present invention is not directed to such unusual structures.

Another patent application WO 00/21552 claims several unusual O-glycan structures isolated from bovine submaxillary mucin. Some of the structures such as GlcNAcβ6GalNAcα6GalNAc and GalNAcβ3(GlcNAcβ6) GalNAc comprise terminal GlcNAc-residues. Present invention is not directed to these structures comprising two Gal- NAc-residues. The application contains speculation about potential therapeutic use of the structures as antigens related to cancer. It has not been shown that the structures are related to bovine cancer but the structures are present in bovine normal submaxillary secretion. Moreover, it is even less probable that the structures would be present in human tissues, as the glycosylations are species specific and vary between human and bovine, so that glycosyltransferase and glycosylation profiles are different in bovine and human. The human genome is also known and glycosyltransferases which could be related to synthesis of the claimed bovine structures has not been produced and characterized. So far none of the six novel glycosyltransferases claimed has been described from human, or human cancer (nor from bovine cancer). Moreover, any bovine glycosylations has not been found from human salivary mucins which have been carefully characterized.

SUMMARY OF THE INVENTION

The present invention describes oligosaccharide sequences, which are specifically expressed by human tumors. The present invention is related to a method of determining an oligosaccharide sequence, which comprises a tumor specific terminal N-acetylglucosamine residue, in a biological sample, the presence of said sequence in said sample being an indication of the presence of cancer. The present invention provides antigenic substances comprising said oligosaccharide sequences in a polyvalent form and it further provides diagnostic agents, pharmaceutical compositions and cancer vaccines comprising said oligosaccharide sequences or substances binding to said oligosaccharide sequences. The present invention is also related to methods for the treatment of cancer.

DETAILED DESCRIPTION OF THE INVENTION

Figure 1:
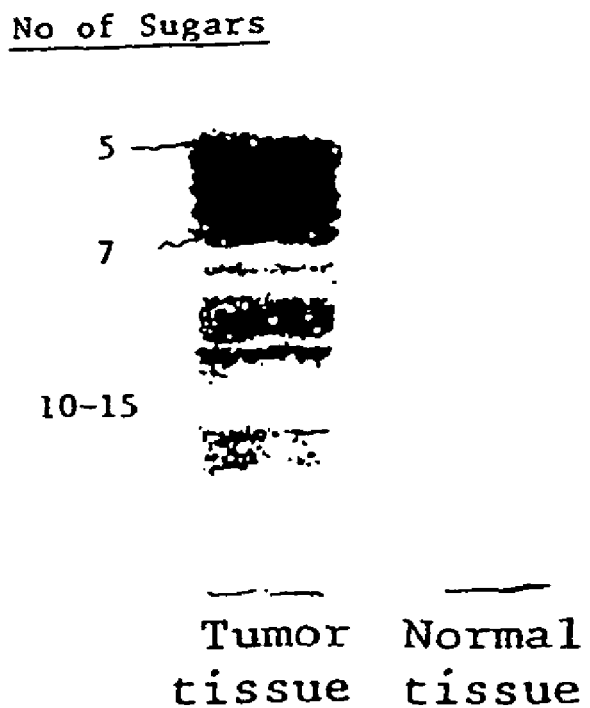
FIG. 1. An autoradiogram of a thin-layer assay after overlayering and binding of GlcNAcβ-specific *E. coli* bacterium demonstrating the tumor specificity of the oligosaccharide sequences containing terminal GlcNAc residue: non-acidic glycosphingolipids from hypernephroma tumor (first lane) and corresponding glycosphingolipid fraction from normal kidney (second lane).

Present invention is directed to terminal β-linked N-acetylglucosamine oligosaccharide chain structures and protein linked monosaccharide N-acetylglucosamine which are presented by human tumors. The present invention realizes specific defects in human tumors, which lead to cell surface and extracellular presentation of unusual carbohydrates comprising terminal N-acetylglucosamines. In general, the terminal GlcNAc-structures are very rare in human normal tissues. The expression of the structures are caused by two factors. For the first the biosynthesis and degradation machinery in the tumor cells does not work properly. Many terminal structures in normal tissues comprise galactose on GlcNAc-residues, these structures are capped by sialic acids, blood group antigens and the like. The present data indicates that the cancer carbohydrates are exposed to unusual glycosidase activities and the defective glycosylation reactions by β4- and possibly also by β3-galactosyltransferases. Defects were observable in all 3 types of β-galactosylated oligosaccharide sequences. Secondly the intracellular targeting and quality control of glycosylation including glycoprotein and glycolipid structures seem to be defective. In normal cells the glycosylation is under quality control which recirculates underglycosylated proteins and glycolipids to complete the natural glycosylation, so that in normal cells the amount of the structures according to the invention are very rare on cell surfaces. In normal cells or tissues the oligosaccharide structures described by the invention are present in low amounts in human golgi apparatus, the known protein linked GlcNAc is considered almost exclusively as cytoplasmic and nuclear protein modification. The defects in organization of the golgi apparatus leads to partial cell surface expression of the tumor specific structures described by the present invention. In a specific embodiment the present invention is specifically directed to cell surface or tissue surface forms of the tumor associated GlcNAc-structures according to the invention. Even intracellularily overexpressed structures according to the present invention are directly useful for diagnostic applications.

The defects in galactosylation and presence of unusual glycosidase activities and loss of intracellular control lead to three types of tumor associated glycosylations:

1. incomplete, undergalactosylated protein linked N-glycans;
2. incomplete, undergalactosylated O-glycan core structures,
3. undergalactosylated polylactosamines, as exemplified by a poly-N-acetyllactosamine type glycolipid from human hypernephroma.

These defects lead to several unusual terminal epitopes on glycoproteins and glycolipids. The present invention is directed to the three groups of oligosaccharide epitopes. The current invention notices for the first time similar general defect on all three types of glycan chains carrying normally β-galactosylated oligosaccharide sequences. Terminal β-linked GlcNAc is present as terminal structure. The structures indicate defects in enzymatic steps directly modifying the terminal GlcNAc-residues including β1,4(3)-Gal-transferase reactions and on the other hand increased glycosidase activities in the Golgi-pathway which could degrade terminal structures. However, the generality of the defect in the three types of carbohydrates would indicate that organization of the golgi apparatus is so disturbed that terminally modifying enzymes located in late golgi cannot effectively modify all glycans expressed by tumor cells.

Furthermore, present invention discloses 4. missdirected expression of protein linked N-acetylglucosamine monosaccharide on cancers and tumors.

The protein linked N-acetylglucosamine is in general present in so called O-GlcNAc-structures intracellularily. The inventors have noticed strong overexpression of the protein linked N-acetylglucosamine. The over-expression leads to even some cell surface associated labeling of the O-linked GlcNAc on human tumors.

Though the terminal β-linked GlcNAc is common to the all three groups 1-3, it is realized that the subterminal structures have effect on the structures which should be recognized in diagnostic or therapy of tumors or cancers. The present invention is specifically directed to therapeutic and diagnostic uses of terminal oligosaccharide sequences comprising the terminal GlcNAc and one to several neighboring monosaccharide residues in the three defective oligosaccharide sequence groups. The present invention is directed to the oligosaccharide sequences comprising nonreducing end terminal β-GlcNAc oligosaccharide sequences on polylactosamines, or O-glycans or N-glycans.

1. Incomplete, Undergalactosylated or Degraded N-Linked Glycans

The inventors have characterized by mass spectrometry several N-glycan structures comprising terminal GlcNAc residues from tumors such as larynx, stomach, colon and lung tumors. The present invention shows that the overexpression of the N-glycans on tumors is common. The novel N-glycan type tumor antigens were also detected specifically by novel glycosyltransferase methods from tissue sections of tumors but not or in lower amounts in corresponding normal or non-malignant tissues.

The present invention is directed to N-glycan structure GlcNAcβ2Manα3(GlcNAcβ2Manα6)Manβ4GlcNAcβ4 (Fucα6)GlcNAcβAsn and oligosaccharide substructures thereof carrying non-reducing end protein or peptide linked terminal GlcNAc. Asn indicates asparagines amino acid directly linked to the protein in the natural antigen. The natural protein linked oligosaccharide sequence in tumor bound form should contain the reducing end GlcNAcβAsn-structure to be used according to the present invention and at least one of the branches carrying the terminal GlcNAcβ2Man. When the N-glycan structure is used for making antigenic epitopes, the present invention is directed to at least one of natural oligosaccharide sequence structures and structures truncated from the reducing end of the N-glycan according to the Formula

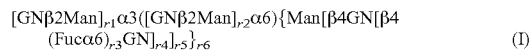  (I)

wherein r1, r2, r3, r4, r5, and r6 are either 0 or 1, with the proviso that at least r1 is 1 or r2 is 1.

GN is GlcNAc, with the proviso that when both r1 and r2 are 1, one GNβMan can be further elongated with one or several other monosaccharide residues such as by galactose, and/or one GNβ2Man can be truncated to Man, and/or Manα6 residue and/or Manα3 residues can be further substituted by GNβ6 or GNβ4, and/or Manβ4 can be further substituted by GNβ4. { } indicates groups either present or absent in a linear sequence. ( ) indicates branching.

The structures represent truncated forms of known N-linked glycan structures on human N-glycans. Such structures are rare on normal tissues and therefore the structures are suitable for immunodiagnostics.

A group of more preferred structures are represented by formula:

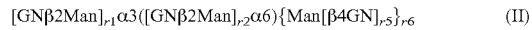  (II)

wherein r1, r2, r5, and r6 are either 0 or 1, with the proviso that at least r1 is 1 or r2 is 1.

GN is GlcNAc, with the proviso that when both r1 and r2 are 1, one GNβMan can be further elongated with one or several other monosaccharide residues such as by galactose, and/or one GNβ2Man can be truncated to Man, and/or Manα6 residue and/or Manα3 residues can be further substituted by GNβ6 or GNβ4, and/or Manβ4 can be further substituted by GNβ4. In a more preferred embodiment GN is GlcNAc, with the proviso that when both r1 and r2 are 1, one GNβMan can be further elongated one or several other monosaccharide residues such as by galactose, and/or one GNβ2Man can be truncated to Man, and/or Manα6-residue, and most preferably GN is GlcNAc.

The preferred non-elongated structures include:
GlcNAcβ2Man, GlcNAcβ2Manα3(GlcNAcβ2Manα6)Man, GlcNAcβ2Manα3(GlcNAcβ2Manα6)Manβ4GlcNAc, GlcNAcβ2Manα3(GlcNAcβ2Manα6) Manβ4GlcNAcβ4GlcNAc, GlcNAcβ2Manα3 (GlcNAcβ2Manα6)Manβ4GlcNAcβ4(Fucα6)GlcNAc, GlcNAcβ2Manα3(Manα6)Man, GlcNAcβ2Manα3 (Manα6)Manβ4GlcNAc, GlcNAcβ2Manα3(Manα6) Manβ4GlcNAcβ4GlcNAc, GlcNAcβ2Manα3(Manα6) Manβ4GlcNAcβ4(Fucα6)GlcNAc, Manα3 (GlcNAcβ2Manα6)Man, Manα3(GlcNAcβ2Manα6) Manβ4GlcNAc, Manα3(GlcNAcβ2Manα6) Manβ4GlcNAcβ4GlcNAc, Manα3(GlcNAcβ2Manα6) Manβ4GlcNAcβ4(Fucα6)GlcNAc, GlcNAcβ2Manα3Man, GlcNAcβ2Manα3Manβ4GlcNAc,
GlcNAcβ2Manα3Manβ4GlcNAcβ4GlcNAc,
GlcNAcβ2Manα3Manβ4GlcNAcβ4(Fucα6)GlcNAc,
GlcNAcβ2Manα6Man, GlcNAcβ2Manα6Manβ4GlcNAc,
GlcNAcβ2Manα6Manβ4GlcNAcβ4GlcNAc,
GlcNAcβ2Manα6Manβ4GlcNAcβ4(Fucα6)GlcNAc.

More preferred N-glycan oligosaccharide sequences include:
GlcNAcβ2Man, GlcNAcβ2Manα3(GlcNAcβ2Manα6)Man,
GlcNAcβ2Manα3(GlcNAcβ2Manα6)Manβ4GlcNAc,
GlcNAcβ2Manα3(Manα6)Man, GlcNAcβ2Manα3 (Manα6)Manβ4GlcNAc, Manα3(GlcNAcβ2Manα6)Man,
Manα3(GlcNAcβ2Manα6)Manβ4GlcNAc,
GlcNAcβ2Manα3Man, GlcNAcβ2Manα3Manβ4GlcNAc,
GlcNAcβ2Manα6Man, GlcNAcβ2Manα6Manβ4GlcNAc.

And most preferred N-glycan oligosaccharide sequences include:
GlcNAcβ2Man, GlcNAcβ2Manα3(GlcNAcβ2Manα6)Man,
GlcNAcβ2Manα3(GlcNAcβ2Manα6)Man4GlcNAc,
GlcNAcβ2Manα3(Manα6)Man, GlcNAcβ2Manα3 (Manα6)Manβ4GlcNAc, Manα3(GlcNAcβ2Manα6)Man,
Manα3(GlcNAcβ2Manα6)Manβ4GlcNAc.

2. Incomplete, Undergalactosylated or Degraded O-Linked Glycans

The inventors have also found out that O-glycans of tumors contain structures carrying terminal β-linked GlcNAc. The O-glycan specificity for tumor is demonstrated in the examples by describing specific natural cancer associated antibody from a person recovered from ovarian cancer and by absence of the antibody in pool of sera from persons without cancer background.

The present invention is also directed to human tumor specific O-glycan core structures comprising terminal P-linked GlcNAc residues, preferably with the provision that the O-glycan sequences do not comprise GalNAc-GalNAc sequence. The preferred O-glycan oligosaccharide sequences comprises at least one oligosaccharide sequence according to the formula:

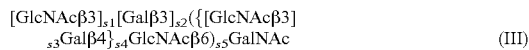

[GlcNAcβ3]$_{s1}$[Galβ3]$_{s2}$({[GlcNAcβ3]$_{s3}$Galβ4}$_{s4}$GlcNAcβ6)$_{s5}$GalNAc  (III)

wherein s1, s2, s3, s4 and s5 are independently 0 or 1, with the proviso that at least s1 is 1 or s5 is 1 and s3 and s4 are 1 or s5 is 1 and s3 and s4 are 0, so that the oligosaccharide sequence comprises at least one nonreducing end terminal GlcNAcβ- residue.

More preferred O-glycan structures include at least one structure according to the formula:

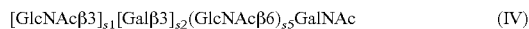

[GlcNAcβ3]$_{s1}$[Galβ3]$_{s2}$(GlcNAcβ6)$_{s5}$GalNAc  (IV)

wherein s1, s2, and s5 are independently 0 or 1, with the proviso that at least s1 is 1 or s5 is 1.

Preferred O-glycan oligosaccharide sequences include:
Galβ3(GlcNAcβ3Galβ4GlcNAcβ6)GalNAc,
GlcNAcβ3Galβ4GlcNAcβ6GalNAc, GlcNAcβ3Galβ3 (Galβ4GlcNAcβ6)GalNAc, GlcNAcβ3Galβ3(GlcNAcβ6) GalNAc, GlcNAcβ3Galβ3GalNAc, Galβ3(GlcNAcβ6)GalNAc, GlcNAcβ3(GlcNAcβ6)GalNAc, GlcNAcβ6GalNAc, GlcNAcβ3GalNAc.

More preferably O-glycan oligosaccharide sequences include:
Galβ3(GlcNAcβ3Galβ4GlcNAcβ6)GalNAc,
GlcNAcβ3Galβ4GlcNAcβ6GalNAc,
GlcNAcβ3Galβ3GalNAc, Galβ3(GlcNAcβ6)GalNAc,
GlcNAcβ6GalNAc and GlcNAcβ3GalNAc.

Most preferred O-glycan sequences include Galβ3 (GlcNAcβ6)GalNAc, GlcNAcβ6GalNAc.

The present invention is specifically directed to human antibodies recognizing O-glycan oligosaccharide sequence structures Galβ3(GlcNAcβ6)GalNAc, and/or GlcNAcβ6GalNAc but not Galβ3(Galβ4GlcNAcβ6)GalNAc, and/or Galβ4GlcNAcβ6GalNAc and therapeutic and diagnostic uses of these as described by the present invention. In a preferred embodiment the present invention is directed to human antibody recognizing effectively oligosaccharide sequence Galβ3(GlcNAcβ6)GalNAc but not oligosaccharide sequence Galβ3(Galβ4GlcNAcβ6)GalNAc. In preferred embodiment the human antibody is natural antibody. In another embodiment the antibody is induced by a cancer vaccine. In more preferred embodiments the human antibody is an IgG or IgA or IgM antibody, most preferably a IgG antibody.

As separate embodiment the present invention is directed to uses of to rare sialylated variants of the O-glycan core structures such as GlcNAcβ3(NeuNAcα6)GalNAc or NeuNAcα3Galβ3(GlcNAcβ6)GalNAc.

3. Poly-N-acetylactosamine Type Sequences Containing Terminal GlcNAcβ3 and/or GlcNAcβ6

The present invention describes the presence of terminal N-acetylglucosamine (GlcNAc) on poly-N-acetylactosamine type structures on human tumors. The structures were first found in large amounts from a human hyper nephroma tumor in one out of four tumors studied. The glycolipid fraction of the tumor was characterized to contain terminal N-acetylglucosamines by a specific radiolabelled *Escherichia coli* strain and FAB-mass spectrometry of permethylated sample. The glycolipid fraction also contained terminal N-acetyllactosamines, which could be detected by using a specific lectin. Screening of normal kidney glycolipids by the bacterium showed that the terminal GlcNAc was not present in the corresponding normal tissue, as it was not present in several other control tissues. One embodiment of the present invention describes detection or isolation of an oligosaccharide sequence or oligosaccharide sequences comprising a terminal N-acetylglucosamine residue from tumor.

Following saccharide sequences are among the tumor specific structures to be isolated or detected: GlcNAcβ3Gal, GlcNAcβ3Galβ4GlcNAc, GlcNAcβ6Gal, GlcNAcβ3 (GlcNAcβ6)Gal, GlcNAcβ3(GlcNAcβ6)Galβ4GlcNAc, GlcNAcβ6Gal or GlcNAcβ6Galβ4GlcNAc, the sequences are part of poly-N-acetyllactosamine chains so that the chains comprise at least one terminal β-linked GlcNAc.

In a more preferred embodiment the present invention is directed to non-β6-containing linear polylactosamine sequences: GlcNAcβ3Gal, GlcNAcβ3Galβ4GlcNAc, GlcNAcβ3Galβ4GlcNAc3Galβ4GlcNAc.

In a separate embodiment the present invention is directed to β6-containing non-branched polylactosamine sequences: GlcNAcβ6Gal, GlcNAcβ6Galβ4GlcNAc, GlcNAcβ6Galβ4GlcNAc3Galβ4GlcNAc.

A preferred group of poly-N-acetylactosamine type sequences are β3-, β6-branched structures, GlcNAcβ3 (GlcNAcβ6)Gal, GlcNAcβ3(GlcNAcβ6)Galβ4GlcNAc, Galβ4GlcNAcβ3(GlcNAcβ6)Galβ4GlcNAc. Then branched structures resemble branched O-glycan structures.

Structures with type one N-acetyllactosamine, GlcNAcβ3Galβ3GlcNAc, or GlcNAcβ6Galβ3GlcNAc are also among the compounds within the scope of the invention.

4. Protein Linked N-acetylglucosamine

The inventors have characterized protein linked GlcNAc residues from tumors such as larynx, stomach, colon and lung tumors. The present invention shows that the overexpression of the protein linked GlcNAc expression on tumors is common. The novel N-glycan type tumor antigens were also detected specifically by novel glycosyltransferase methods from tissue sections of tumors but not or in lower amounts in corresponding normal or non-malignant tissues. The analysis of the protein linked GlcNAc indicated presence of several forms of protein linked GlcNAc.

In a specific embodiment the present invention is directed according to the present invention to therapeutic, and diagnostic uses, and pharmaceutical compositions, comprising beta linked N-acetylglucosamine monosaccharide residue, GlcNAcβ. Most of the tumors cells carry the O-glycan like GlcNAc releasable by β-elimination.

The present invention is in a preferred embodiment directed to the diagnostic and therapeutic uses according to the present invention using O-glycosidic structures GlcNAc-Ser and/or GlcNAcThr,
wherein the hydroxyl groups serine and threonine residues are glycosidically linked to the GlcNAc residue. The serine (Ser) and threonine (Thr) amino acid residues are in a preferred embodiments parts of peptides or peptide conjugates or derivatized from amino- and/or carboxylic acid groups.

In another preferred embodiment the present invention is directed to the uses of GlcNAcX, wherein X is aglycon preferably mimicking serine or threonine amino acid residues described above.

In a preferred embodiment GlcNAcβSer and/or GlcNAcβThr, GlcNAcβX is linked to polyvalent carrier according to the present invention for uses described by the invention, preferably to a carrier useful for vaccination, and most preferably to a carbohydrate carrier as described by the present invention.

In another preferred embodiment GlcNAcαSer and/or GlcNAcαThr, GlcNAcαX is linked to polyvalent carrier according to the present invention, preferably to a carrier useful for vaccination, and most preferably to a carbohydrate carrier as described by the present invention.

The present invention is also directed β-linked N-glycosidic analogs of the O-glycan type structures described above, for example GlcNAcβ-Asn and peptide derivatives and analogs thereof. In biological samples such structures are formed by exoglycosidases or by endo-N-acetylglucosaminyltransferase.

General Structures Representing Oligosaccharide Sequences According to the Invention The oligosaccharide sequences of the invention can be a part of a glycolipid, a part of a glycoprotein, and/or a part of a N-acetyllactosamine chain. The tumor specific oligosaccharide sequences can also be a part of glycolipids, a part of N-linked glycans or O-linked glycans of glycoproteins. The tumor associated oligosaccharide sequences can also be directly linked to O-glycosidic GalNAc. Defects or changes in biosynthetic and/or biodegradative pathways of tumors lead to the synthesis of the oligosaccharide sequences of the invention both on glycolipids and glycoproteins. Terminal N-acetylglucosamine means that the non-reducing end GlcNAc residue in an oligosaccharide chain is not substituted by any other monosaccharide. The term oligosaccharide sequence indicates that the monosaccharide residue/residues in the sequence are part of a larger glycoconjugate, which contains other monosaccharide residues in a chain, which may be branched, or natural substituted modifications of oligosaccharide chains. The oligosaccharide chain is normally conjugated to a lipid anchor or to a protein. In a preferred embodiment the oligosaccharide sequences according to the present invention are non-reducing terminal oligosaccharide sequences, which means here that the oligosaccharide sequences are not linked to other monosaccharide or oligosaccharide structures except optionally from the reducing end of the oligosaccharide sequence. The oligosaccharide sequence when present as conjugate is preferably conjugated from the reducing end of the oligosaccharide sequence, though other linkage positions which are tolerated by the antibody/binding substance binding can also be used. In a more specific embodiment the oligosaccharide sequence according to the present invention means the corresponding oligosaccharide residue which is not linked by natural glycosidic linkages to other monosaccharide or oligosaccharide structures. The oligosaccharide residue is preferably a free oligosaccharide or a conjugate or derivative from the reducing end of the oligosaccharide residue.

Uses described for the terminal GlcNAc oligosaccharide chain by the invention for the N-linked, O-linked and polylactosamine type oligosaccharide sequences described also apply to the monosaccharide protein linked GlcNAc and derivatives thereof as described.

Minor species of ganglio- or galactosylglobosides can also represent the tumor specific terminal GlcNAc: terminal Galβ4GlcNAcβ3/β6 structures are linked to the glycolipid cores in some tissues and under low galactosylation conditions described by the invention terminal GlcNAcs can be revealed.

In another embodiment of the invention the tumor specific oligosaccharides are detected for the diagnostics of tumor.

Term "oligosaccharide sequence" or "oligosaccharide" means herein also the protein linked GlcNAc and derivatives thereof as described.

Preferably the tumor specific oligosaccharide sequence is detected by a specific binding substance which can be an aptamer, lectin, peptide, or protein, such as an antibody, a fragment thereof or genetically engineered variants thereof. More preferably the specific binding substance is divalent, oligovalent or polyvalent. Most preferably the binding substance is a lectin or an antibody.

Specific binding combinatorial chemistry libraries can be used to search for the binding molecules. Saccharide binding proteins, antibodies or lectins can be engineered, for example, by phage display methods to produce specific binders for the structures of the invention. Labelled bacteria or cells or other polymeric surfaces containing molecules recognizing the structures can be used for the detection. Oligosaccharide sequences can also be released from tumor cells by endoglycosidase enzymes. Alternatively oligosaccharides can be released by protease enzymes, such as glycopepides. Chemical methods to release oligosaccharides or derivatives thereof include, e.g., otsonolysis of glycolipids and beta-elimination or hydrazinolysis methods to release oligosaccharides from glycoproteins. Alternatively the glycolipid fraction can be isolated. A substance specifically binding to the tumor specific oligosaccharide sequences can also be used for the analysis of the same sequences on cell surfaces. Said sequences can be detected, e.g., as glycoconjugates or as released and/or isolated oligosaccharide fractions. The possible methods for the analysis of said sequences in various forms also include NMR-spectroscopy, mass spectrometry and glycosidase degradation methods. Preferably at least two analysis methods are used, especially when methods of limited specificity are used.

The present invention is also directed to the use of the tumor specific oligosaccharide sequences or analogs or derivatives thereof to produce polyclonal or monoclonal antibodies recognizing said structures using following process: 1) producing synthetically or biosynthetically a polyvalent conjugate of an oligosaccharide sequence of the invention or analogue or derivative thereof, the polyvalent conjugate being, for instance, according to the following structure: position C1 of the reducing end terminal of an oligosaccharide sequence (OS) comprising the tumor specific terminal sequence of the invention is linked (-L-) to an oligovalent or a polyvalent carrier (Z), via a spacer group (Y) and optionally via a monosaccharide or oligosaccharide residue (X), forming the following structure

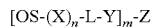

[OS-(X)$_n$-L-Y]$_m$-Z where integer m have values m>1 and n is independently 0 or 1; L can be oxygen, nitrogen, sulfur or a carbon atom; X is preferably lactosyl-, galactosyl-, poly-N-acetyl-lactosaminyl, or part of an O-glycan or an N-glycan oligosaccharide sequence, Y is a spacer group or a terminal conjugate such as a ceramide lipid moiety or a linkage to Z; 2) immunizing an animal or human with polyvalent conjugate together with an immune response activating substance. Preferably the oligosaccharide sequence is polyvalently conjugated to an immune response activating substance and the conjugate is used for immunization alone or together with an additional immune response activating substance. In a preferred embodiment the oligosaccharide conjugate is injected or administered mucosally to an antibody producing organism with an adjuvant molecule or adjuvant molecules. For antibody production the oligosaccharide or analogs or derivatives thereof can be polyvalently conjugated to a protein such as BSA, keyhole limpet hemocyanin, a lipopeptide, a peptide, a bacterial toxin, a part of peptidoglycan or immunoactive polysaccharide or to another antibody production activating molecule. The polyvalent conjugates can be injected to an animal with adjuvant molecules to induce antibodies by routine antibody production methods known in the art.

Antibody production or vaccination can also be achieved by analogs or derivatives of the tumor specific oligosaccharide sequences. Simple analogs of the N-acetyl-group containing oligosaccharide sequences include compounds with modified N-acetyl groups, for example, N-alkyls, such as N-propanyl.

Analogs that can be used for the production of antibodies binding GlcNAcβ3Galβ4GlcNAc include sequences Hex(NAc)$_{0-1}$α3Galβ4GlcNAc, Hex(NAc)$_{0-1}$β3Galβ4GlcNAc, where Hex is hexose, preferably Gal or Glc. The analogs may also comprise molecules where GlcNAc is replaced by a close isomer such as ManNAc.

According to the invention it is possible to use the tumor specific oligosaccharide sequences for the purification of antibodies from serum, preferably from human serum. Normally there are large amounts of antibodies recognizing terminal GlcNAc structures in human serum. There is also a class of natural antibodies recognizing terminal Galα3Galβ4GlcNAc structures. The Gala antigen is not naturally present in human and recently it was shown that the natural antibodies also bind in vitro structures GalNAcα3Galβ4GlcNAc, GalNAcβ3 Galβ4GlcNAc, and GlcNAcβ3Galβ4GlcNAc (Teneberg et al., 1996). The X2-structure, GalNAcβ3Galβ4GlcNAc, is a normal antigen on human tissues and structures GalNAcα3Galβ4GlcNAc and Galα3Galβ4GlcNAc have not been described from human normal or cancer tissues. Thus, the present finding that the terminal GlcNAc-structure is a tumor antigen indicated that it is possible that the actual function of the natural antibodies is to prevent cancers and destroy tumors having terminal GlcNAc-structures. The tumor specific oligosaccharides or derivatives or analogs, such as a close isomer, can also be immobilized for the purification of antibodies from serum, preferably from human serum. The present invention is directed to natural human antibodies which bind strongly to the tumor specific oligosaccharide sequences according to the present invention.

The tumor specific oligosaccharide sequences can also be used for detection and or quantitation of the human antibodies binding to the tumor specific oligosaccharide sequences, for example, in enzyme-linked immunosorbent assay (ELISA) or affinity chromatography type assay formats. The detection of human antibodies binding to the tumor specific oligosaccharide sequences is preferably aimed for diagnostics of cancer, development of cancer therapies, especially cancer vaccines against the oligosaccharide sequences according to the present invention, and search for blood donors which have high amounts of the antibodies or one type of the antibody.

Furthermore, it is possible to use human antibodies or humanized antibodies against the tumor specific oligosaccharide sequences to reduce the growth of or to destroy a tumor or cancer. Human antibodies can also be tolerated analogs of natural human antibodies against the tumor specific oligosaccharide sequences; the analogs can be produced by recombinant gene technologies and/or by biotechnology and they may be fragments or optimized derivatives of human antibodies. Purified natural anti-tumor antibodies can be administered to a man without any expected side effect as such antibodies are transferred during regular blood transfusions. This is true under conditions that the tumor specific structures are not present on normal tissues or cells and do not vary between individuals as blood group antigens do, however, such blood-group-like variations are not known for the structures with terminal GlcNAc. In another embodiment of the invention species specific animal antibodies are used against a tumor or cancer of the specific animal. The production of specific humanized antibodies by gene engineering and biotechnology is also possible: the production of humanized antibodies has been described in U.S. Pat. Nos. 5,874,060 and 6,025,481, for example. The humanized antibodies are designed to mimic the sequences of human antibodies and therefore they are not rejected by immune system as animal antibodies are, if administered to a human patient. It is realized that the method to reduce the growth of or to destroy cancer applies both to solid tumors and to cancer cells in general. It is also realized that the purified natural human antibodies recognizing any human cancer specific antigen, preferably an oligosaccharide antigen, can be used to reduce the growth of or to destroy a tumor or cancer. In another embodiment species specific animal antibodies are used against a tumor or cancer of the specific animal.

According to the invention human antibodies or humanized antibodies against the tumor specific oligosaccharide sequences, or other tolerated substances binding the tumor specific oligosaccharide sequences, are useful to target toxic agents to tumor or to cancer cells. The toxic agent could be, for example, a cell killing chemotherapeutics medicine, such as doxorubicin (Arap et al., 1998), a toxin protein, or a radiochemistry reagent useful for tumor destruction. Such therapies have been demonstrated and patented in the art. The toxic agent may also cause apoptosis or regulate differentiation or potentiate defence reactions against the cancer cells or tumor. In another embodiment of the invention species specific animal antibodies are used against a tumor or cancer of the specific animal. The cancer or tumor binding antibodies according to the present invention can be also used for targeting prodrugs active against tumor or enzymes or other substances converting prodrugs to active toxic agents which can destroy or inhibit tumor or cancer, for example in so called ADEPT-approaches.

The therapeutic antibodies described above can be used in pharmaceutical compositions for the treatment or prevention of cancer or tumor. The method of treatment of the invention can also be used when patient is under immunosuppressive medication or he/she is suffering from immunodeficiency.

The terminal GlcNAc, or preferably GlcNAcβ3/6Galβ4GlcNAc-type cancer or tumor glycosylation, may be more common in tumors occurring in patients suffering from immunodeficient conditions, e.g., immunodeficiency causing diseases, such as AIDS, or immunodefiency caused by immunosuppressive medication. Kaposi's sarcoma is a common cancer related to AIDS and immunodeficiency. Immunosuppressive medications are used, for instance, with organ transplantations to prevent rejection during kidney, heart, liver or lung transplantations. Malignancies arising during such therapies are in general benign, but they cause often the loss of the precious organ transplant. Some of the potential natural anticancer antibodies may probably also recognize following epitopes: GalNAcβ3Galβ4GlcNAc, GalNAcα3Galβ4GlcNAc, and Galα3Galβ4GlcNAc, which have been shown to be similar. The first structure, $X_2$, is more common in persons who belong to a rare variant of p-blood group, these persons may also have less antibodies recognizing GlcNAcβ3Galβ4GlcNAc structure. Capability to produce antibodies against tumor or cancer specific antigens may vary according to individual differences in immune system. Persons who have recovered from cancer may have especially high amounts of natural anti-cancer antibodies.

A possible example from the antibody mediated immune reaction against tumor tissue is a total recovery from hypernephroma after surgery of the majority of the tumor. The oligosaccharide sequences with terminal GlcNAcs are potential targets of such immune response.

Other Methods for Therapeutic Targeting of Tumors

It is realized that numerous other agents beside antibodies, antibody fragments, humanized antibodies and the like can be used for therapeutic targeting of cancer or tumors similarity with the diagnostic substances. It is specifically preferred to use non-immunogenic and tolerable substances to target cancer or tumor. The targeting substances binding to the cancer or tumor comprise also specific toxic or cytolytic or cell regulating agents which leads to destruction or inhibition of cancer or tumor. Preferably the non-antibody molecules used for cancer or tumor targeting therapies comprise molecules specifically binding to the cancer or tumor specific oligosaccharide sequences according to the present invention are aptamers, lectins, genetically engineered lectins, enzymes recognizing the terminal GlcNAc-structures such as glycosidases and glycosyltransferase and genetically engineered variants thereof. Labelled bacteria, viruses or cells or other polymeric surfaces containing molecules recognizing the structures can be used for the cancer or tumor targeting therapies. The cancer or tumor binding non-antibody substances according to the present invention can also be used for targeting prodrugs against cancer or tumor to a cancer or tumor or for targeting enzymes or other substances converting prodrugs to active toxic agents which can destroy or inhibit cancer or tumor.

Targetting Terminal GlcNAc-Comprising Tumor Antigens by Glycosyltransferases

The present invention is specifically directed to novel method to transfer a modified monosaccharide derivative on cancer cells or tumor for treatment or diagnostics. We disclose a method of generating a covalent bond between a toxic agent, label, drug or immunologically active carbohydrate and the surface of a pathogenic cell of a patient, which surface comprises an acceptor structure recognized by a transferase enzyme, comprising the steps of conjugating said toxic agent, label, drug or immunologically active carbohydrate with a donor molecule of the transferase enzyme, and (a) administering the conjugate obtained and optionally said transferase enzyme to the patient for the treatment of tumor or (b), for tumor diagnostics, contacting the conjugate obtained to a tumor sample and detecting said label.

The monosaccharide derivatives to be transferred by glycosyltransferases also comprise a glycosidically linked nucleotide residue. The preferred monosaccharide derivatives are 2-modified such as Amide derivatives of UDP-galactosamine Preferred therapeutic or diagnostic monosaccharide derivative is UDP-GalN[-S]-D, wherein S is an optional spacer group D is derivatizing group including molecular labels such as for example biotin or a fluorescent molecule including, or a toxic agent, prodrug or prodrug releasing substance as described for other cancer or tumor targeting methods.

The spacer is preferably flexible enough to allow the binding of the modified nucleotide monosaccharide to the transferase.

A preferred monosaccharide derivative is UDP-N-(6-biotinamidohexanoyl)galactosamine. A preferred enzyme to be used is a galactosyltransferase which is engineered to transfer effectively 2-modified monosaccharides. Also natural GalNAc/GlcNAc-transferases with similar specificity from animals for example, may also be used.

The present invention is especially directed to method to label tumor tissue by biotin by incubating the tissue with UDP-GalN-spacer-biotin and a modified galactosyltransferase.

The present invention is in a separate embodiment directed to a diagnostic method in which 1. radiolabelled Gal is transferred from radiolabelled UDP-Gal to human tumor tissue by galactosyltransferase, preferably by β4-galactosyltransferase and 2. the radioactivity incorporated to the tissue is used to determine amount of terminal GlcNAc residues on the tumor.

The methods using galactosyltransferases for labelling are effective for all types of terminal β-GlcNAc structures of the present invention.

Use of Antibodies, Preferably from Animals, in Gastrointestinal and Food Related Applications The present invention is specifically directed to the use of substances and antibodies binding to tumor specific oligosaccharide sequences according to the present invention for therapies in gastrointestinal tract of the patient, preferably in human patient. The therapeutic antibodies for use in human gastrointestinal tract may be antibodies produced by animals for example antibodies in milks of domestic animals, for example in milk of domestic ruminants such as cows, sheep, goat or buffalo or antibodies produced in hen eggs. The animals can be immunized tumor specific carbohydrate conjugates as known in the art. The present invention is also directed to other acceptable, preferably food acceptable proteins which can be used inhibition or destruction of tumors in human gastrointestinal tract, such substances includes plant lectins which are specific for the tumor specific oligosaccharide sequences. The present invention is directed to functional foods and food additives containing antibodies recognizing the tumor specific oligosaccharide sequences according to the present invention in gastrointestinal tract, the present invention is directed also to the use of other food acceptable substances especially lectins binding to the tumor specific oligosaccharide sequences of gastrointestinal tract in functional foods or as food additives.

Screening of Substances Binding to the Tumor Specific Terminal GlcNAcs

The present invention is specifically directed to the use of the tumor specific terminal-GlcNAc-oligosaccharide sequences for the screening of specific binders with regard to the structures. The screening allows finding of optimal binding substances for the tumor specific oligosaccharide sequences according to the present invention. The specific binders may be therapeutic or diagnostic antibodies or other molecules binding to the glycans as described by the present invention above.

The screening of the substances binding to the oligosaccharide sequences according to the invention may be performed in an enzyme linked immonoassays (so called ELISA-assays). Direct binding can be measured for example when either the binding substance or the terminal-GlcNAc-glycan structure is linked to a solid phase matrix.

Free oligosaccharides or oligosaccharide conjugates according to the present invention can be also used as specific inhibitors in the assays. Fluorescence polarization difference and NMR are examples of liquid phase methods to be used for screening of the substances binding to the oligosaccharide sequences according to the invention.

Cancer Vaccines

Furthermore according to the invention the tumor specific oligosaccharide sequences or analogs or derivatives thereof can be used as cancer vaccines in man to stimulate immune response to inhibit or eliminate cancer or tumor cells. The treatment may not necessarily cure cancer but it can reduce tumor burden or stabilize a cancer condition and lower the metastatic potential of cancers. For the use as vaccines the oligosaccharides or analogs or derivatives thereof can be conjugated, for example, to proteins such as BSA or keyhole limpet hemocyanin, lipids or lipopeptides, bacterial toxins such as cholera toxin or heat labile toxin, peptidoglycans, immunoreactive polysaccharides, or to other molecules activating immune reactions against a vaccine molecule. A cancer vaccine may also comprise a pharmaceutically acceptable carrier and optionally an adjuvant. Suitable carriers or adjuvants are, e.g., lipids known to stimulate the immune response. The saccharides or derivatives or analogs thereof, preferably conjugates of the saccharides, can be injected or administered mucosally, such as orally or nasally, to a cancer patient with tolerated adjuvant molecule or adjuvant molecules. The cancer vaccine can be used as a medicine in a method of treatment against cancer or tumor. Preferably the method is used for the treatment of a human patient. Preferably the method of treatment is used for the treatment of cancer or tumor of a patient, who is under immunosuppressive medication or the patient is suffering from immunodeficiency.

Furthermore it is possible to produce a pharmaceutical composition comprising the tumor specific oligosaccharide sequences or analogs or derivatives thereof for the treatment of cancer or tumor. Preferably the pharmaceutical composition is used for the treatment of a human patient. Preferably the pharmaceutical composition is used for the treatment of cancer or tumor, when patient is under immunosuppressive medication or he/she is suffering from immunodeficiency. The methods of treatment or the pharmaceutical compositions described above are especially preferred for the treatment of cancer or tumor diagnosed to express the tumor specific oligosaccharide sequences of the invention. The methods of treatment or the pharmaceutical compositions can be used together with other methods of treatment or pharmaceutical compositions for the treatment of cancer. Preferably the other methods or pharmaceutical compositions comprise cytostatics, anti-angiogenic pharmaceuticals, anti-cancer proteins, such as interferons or interleukins, or a use of radioactivity.

Use of antibodies for the diagnostics of cancer or tumor and for the targeting of drugs to cancer or tumor has been described with other antigens and oligosaccharide structures (U.S. Pat. No. 4,851,511; U.S. Pat. No. 4,904,596; U.S. Pat. No. 5,874,060; U.S. Pat. No. 6,025,481; U.S. Pat. No. 5,795,961; U.S. Pat. No. 4,725,557; U.S. Pat. No. 5,059,520; U.S. Pat. No. 5,171,667; U.S. Pat. No. 5,173,292; U.S. Pat. No. 6,090,789; U.S. Pat. No. 5,708,163; U.S. Pat. No. 5,902,725 and U.S. Pat. No. 6,203,999). Use of cancer specific oligosaccharides as cancer vaccines has also been demonstrated with other oligosaccharide sequences (U.S. Pat. No. 5,102,663; U.S. Pat. No. 5,660,834; U.S. Pat. No. 5,747,048; U.S. Pat. No. 5,229,289 and U.S. Pat. No. 6,083,929).

Combination of the Therapeutic and Diagnostic Methods

Present invention is specifically directed to analysis of abnormal and normal glycosylation structures from human tumors and cancers and use of the analytical information for the production of therapeutic antibodies or cancer vaccines according to the invention. Present invention is specifically directed to treatment of cancer including following steps:

1. analysis of glycosylation of tumor or cancer tissue of a patient
2. analysis of normal glycosylation of the tissue containing the cancer
3. Use of the therapies according to the present invention if the patient has tumor specific oligosaccharide sequences according to the present invention in cancer but does not have the tumor specific oligosaccharide sequences or has these in much lower extent on cell surfaces in the normal tissue.

The data in examples shows the usefulness of the combination of analysis of the tumor specific structures according to the invention, because there are individual variations in glycosylation of tumors and normal tissues. The normal tissue close to tumor may also be contaminated partially contaminated by materials secreted by tumor which may be taken to consideration when analyzing the normal tissue data.

The substance according to the invention can be attached to a carrier. Methods for the linking of oligosaccharide sequences to a monovalent or multivalent carrier are known in the art. Preferably the conjugation is performed by linking the cancer specific oligosaccharide sequences or analogs or derivatives thereof from the reducing end to a carrier molecule. When using a carrier molecule, a number of molecules of a substance according to the invention can be attached to one carrier increasing the stimulation of immune response and the efficiency of the antibody binding. To achieve an optimal antibody production, conjugates larger than 10 kDa carrying typically more than 10 oligosaccharide sequences are preferably used.

The oligosaccharide sequences according to the invention can be synthesized, for example, enzymatically by glycosyltransferases, or by transglycosylation catalyzed by a glycosidase enzyme or a transglycosidase enzyme, for review see Ernst et al., 2000. Specificities of the enzymes and their use of co-factors such as nucleotide sugar donors, can be engineered. Specific modified enzymes can be used to obtain more effective synthesis, for example, glycosynthase is modified to achieve transglycosylation but not glycosidase reactions. Organic synthesis of the saccharides and conjugates of the invention or compounds similar to these are known (Ernst et al., 2000). Carbohydrate materials can be isolated from natural sources and be modified chemically or enzymatically into compounds according to the invention. Natural oligosaccharides can be isolated from milks of various ruminants and other animals. Transgenic organisms, such as cows or microbes, expressing glycosylating enzymes can be used for the production of saccharides. It is possible to incorporate an oligosaccharide sequence according to the invention, optionally with a carrier, in a pharmaceutical composition, which is suitable for the treatment of cancer or tumor in a patient. Examples of conditions treatable according to the invention are cancers in which the tumor expresses one or more of the tumor specific oligosaccharide sequences described in the invention. The treatable cancer cases can be discovered by detecting the presence of the tumor specific oligosaccharide sequences in a biological sample taken from a patient. Said sample can be a biopsy or a blood sample.

The pharmaceutical composition according to the invention may also comprise other substances, such as an inert vehicle, or pharmaceutically acceptable carriers, preservatives etc., which are well known to persons skilled in the art.

The substance or pharmaceutical composition according to the invention may be administered in any suitable way. Methods for the administration of therapeutic antibodies or vaccines are well-known in the art.

The term "treatment" used herein relates to both treatment in order to cure or alleviate a disease or a condition, and to treatment in order to prevent the development of a disease or a condition. The treatment may be either performed in a acute or in a chronic way.

The term "patient", as used herein, relates to any mammal in need of treatment according to the invention.

When a tumor specific oligosaccharide or compound specifically recognizing tumor specific oligosaccharides of the invention is used for diagnosis or typing, it may be included, e.g., in a probe or a test stick, optionally in a test kit. When this probe or test stick is brought into contact with a sample containing antibodies from a cancer patient or cancer cells or tissue of a patient, components of a cancer positive sample will bind the probe or test stick and can be thus removed from the sample and further analyzed.

In the present invention the term "tumor" means solid multicellular tumor tissues. Furthermore the term "tumor" means herein premalignant tissue, which is developing to a solid tumor and has tumor specific characteristics. The term "tumor" is not referring herein to a single cell cancer such as a leukaemia or to cultured cancer cells or a cluster of such cells. The present invention is preferably directed to primary human cancer samples. It is well known that glycosylations in cultivated cancer cells vary and are not in general relevant with regard to cancer. It is also known that transfections, cell culture media and dividing solid tumor to single cells may have dramatic effects for glycosylations. When referring to therapies tumor specific oligosaccharides or oligosaccharide sequences (possibly occasionally referred as cancer specific oligosaccharides/oligosaccharide sequences) are targeted for treatment of all kinds of cancers and tumors. The term cancer includes tumors.

The present invention is specifically directed to the treatment of all types of cancer or tumors expressing the tumor specific oligosaccharide sequences according to the present invention. Examples of preferred cancer types includes cancers of larynx, colon cancer, stomach cancer, ovarian cancer and lung cancer. These cancer types are especially preferred for the N-glycan type terminal GlcNAc related methods and compositions according to the present invention. Lung cancer is a preferred target for the protein linked GlcNAc related methods and compositions according to the present invention. The O-glycan type substances are especially preferred for use in methods and compositions according to the present invention for ovarian cancer and mucinous carcinomas, especially for ovarian adenocarcinomas. In a preferred embodiment the terminal GlcNAc-structures of poly-N-acetyllactosamine type is used for therapy or diagnostics of hypernephroma cancers. The present invention is also specifically directed to the treatment according to the present invention for any type of cancer or tumor which has surface expression of the terminal GlcNAc-structures according to the present invention.

Glycolipid and carbohydrate nomenclature is according to recommendations by the IUPAC-RUB Commission on Biochemical Nomenclature (Carbohydr. Res. 1998, 322:167; Carbohydr. Res. 1997, 297:1; Eur. J. Biochem. 1998, 257:29).

It is assumed that Gal, Glc, GlcNAc, and NeuNAc are of the D-configuration, Fuc of the L-configuration, and that all monosaccharide units are in the pyranose form. Glucosamine is referred as GlcN and galactosamine as GalN. Glycosidic linkages are shown partly in shorter and partly in longer nomenclature, the linkages α3 and α6 of the NeuNAc-residues mean the same as α2-3 and α2-6, respectively, and β1-3, β1-4, and β1-6 can be shortened as β3, β4, and β6, respectively. Lactosamine or N-acetyllactosamine or Galβ3/4GlcNAc means either type one structure residue Galβ3GlcNAc or type two structure residue Galβ1-4GlcNAc, and sialic acid is N-acetylneuraminic acid or NeuNAc, Lac refers to lactose and Cer is ceramide.

The present invention is further illustrated in examples, which in no way are intended to limit the scope of the invention:

EXAMPLES

Example 1

Culturing and Labelling of Bacteria

The recombinant G-fimbriated *Escherichia coli* strain IHE11088 (pRR-5), expressing the GlcNAc-recognizing GafD adhesin (Rhen, M. et al., 1986), was cultured in Luria broth containing tetracyclin (25 µg/ml) and 10 µl [$^{35}$S]-methionine (400 mCi; Amersham Pharmacia Biotech, Little Chalfont, UK) at 37° C. over night. The bacteria were harvested by centrifugation, washed two times with phosphate-buffered saline, pH 7.2 (PBS), and resuspended in PBS to $1 \times 10^9$ CFU/ml. The specific activities were approximately 100 CFU/cpm.

Labelling of *Erythrina cristagalli* Lectin

The Galβ4GlcNAcβ-binding lectin from *Erythrina cristagalli* (Teneberg et al., 1994) was purchased from Vector Laboratories Inc., Burlingame, Calif. Batches of 100 µg protein were labelled with $^{125}$I, using Na$^{125}$I (100 mCi/ml; Amersham Pharmacia Biotech), according to the IODO-GEN protocol of the manufacturer (Pierce, Rockford, Ill.). Approximately $5 \times 10^3$ cpm/µg protein was obtained.

Glycosphingolipid Binding Assays

Binding of radiolabeled bacteria and lectin to glycosphingolipids separated on thin-layer chromatograms was done as reported previously (Teneberg et al., 1994, Hansson et al., 1985). Thin-layer chromatography of glycosphingolipids was performed on aluminium-backed silica gel 60 HPTLC plates (Merck, Darmstadt, Germany), using chloroform/methanol/water 60:35:8 (by volume) as solvent system. Dried chromatograms were dipped for 1 min in diethylether/n-hexane 1:5 (by volume) containing 0.5% (w/v) polyisobutyl-methacrylate (Aldrich Chem. Comp. Inc., Milwaukee, Wis.). After drying, the chromatograms were soaked in PBS containing 2% bovine serum albumin (BSA) (w/v), 0.1% NaN$_3$ (w/v) for 2 hr at room temperature. The chromatograms were subsequently covered with radiolabelled bacteria diluted in PBS ($2-5\times10^6$ cpm/ml) or radiolabelled lectin in BSA ($2\times10^3$ cpm/ml). Incubation was done for 2 hr at room temperature, followed by repeated washings with PBS. The chromatograms were thereafter exposed to XAR-5 X-ray films (Eastman Kodak, Rochester, N.Y.) for 12 hr.

Example 2

Demonstration of Tumor Specificity of Terminal GlcNAc Structure.

Thin-layer overlay assays were performed with radiolabelled G-fimbriated *Escherichia coli* to screen various tumors and normal tissues. The *E. coli* strain IHE11088 (pRR-5) specifically recognizes terminal GlcNAcβ-structures (Rhen, M. et al. 1986). Binding active glycolipids were found in non-acid fraction from one of four hypernephroma tumors studied (FIG. 1). No binding was observed towards corresponding fraction of non-acid glycosphingolipids from human normal kidney or to other control tissues studied.

Example 3

Characterizations of Terminal GlcNAcβ-Structures from Human Hypernephroma

Figure 2:
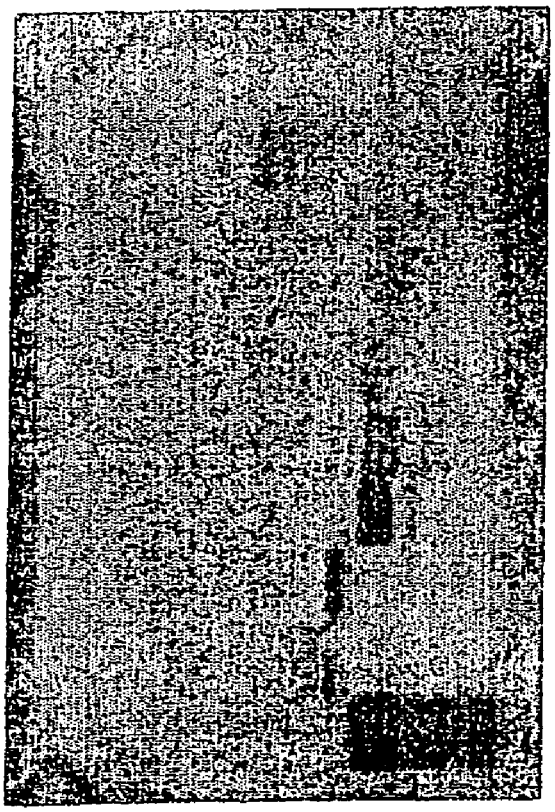
FIG. 2. Thin-layer overlay assays A) using [$^{35}$S]-labelled, GlcNAcβ-specific *E. coli* and B) [$^{125}$I]-labelled Galβ4GlcNAcβ-specific lectin from *Erythrina cristagalli*. Lanes 1-8: Subfractions of non-acid glycosphingolipids from human hypernephroma. Lane 9: Reference glycosphingolipid GlcNAcβ3Galβ4Glcβ1Cer. Lane 10: Reference glycosphingolipid globoside GalNAcβ3Galα4Galβ4Glcβ1Cer.
Figure 2:
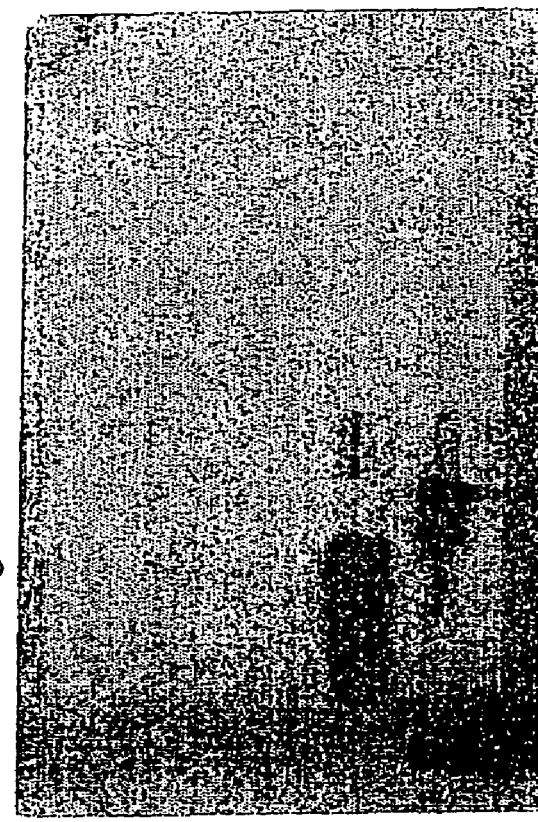

Non-acid glycosphingolipids from human hypernephroma tumor were fractionated and analysed by binding with the GlcNAcβ-specific G-fimbriated *E. coli* (FIG. 1A) and lectin from *Erythrina cristagalli* which recognizes terminal Galβ4GlcNAcβ-structures (FIG. 2B) by thin-layer overlay assay. The two binding reagents show partially overlapping glycospingolipid binding species. The data indicates that the terminal GlcNAc-species are mostly present on N-acetyllactosamine type non-acid glycosphingolipids. The terminal GlcNAc-species which do not have an overlap with lectin binding activity have most probably terminal structures where N-acetyllactosamine is derivatized by GlcNAc such as GlcNAcβ3Galβ3/4GlcNAcβ-; diffuse bands probably also indicates the presence of an isomeric form GlcNAcβ6Galβ3/4GlcNAcβ-. The sample also appears to contain minor species where the terminal GlcNAc and N-acetyllactosamine are present in the same glycolipid. This indicates the presence of branched structures such as Galβ3/4GlcNAcβ3(GlcNAcβ6)Galβ3/4GlcNAcβ- and GlcNAcβ3(Galβ3/4GlcNAcβ6)Galβ3/4GlcNAcβ-; the size distribution of the glycosphingolipids probably also indicates species with two or even more terminal GlcNAcs. The binding of the *Erythrina cristagalli* lectin indicates that most of the lactosamine probably has the type two N-acetyllactosamine structure Galβ4GlcNAc. The glycolipids were partially analyzed by FAB mass spectrometry and by EI masspectrometry after permethylation, which showed presence of terminal HexNAc and that the smallest species with terminal GlcNAc is a pentasaccharide glycosphingolipid probably of lacto or neolacto series. Also 7-meric and larger structures up to 15-mer were observed (FIG. 1). The binding of the lectins indicates that most of the lactosamine probably has the type two N-acetyllactosamine structure.

Example 4

Materials and Methods for Protein Linked Structures and Labeling by Galactosyltransferase Isolation of glycans from formalin-fixed or formalin-fixed and paraffin-embedded tissue samples. Prior to glycan isolation from formalin-fixed samples, proteins were enriched by chloroform-methanol extraction essentially as described in (Manzi et al., 2000). Quantitative extraction of glycoproteins was confirmed by radioactively labelled glycoprotein standards (not shown). Prior to glycan isolation from formalin-fixed and paraffin-embedded samples, the samples were deparaffinised. Glycans were detached from sample glycoproteins by non-reductive β-elimination and purified by chromatographic methods.

MALDI-TOF MS. MALDI-TOF mass spectrometry was performed with a Voyager-DE STR BioSpectrometry Workstation, essentially as in (Saarinen et al., 1999; Papac et al., 1996; Harvey, 1993).

Exoglycosidase digestions. All exoglycosidase reactions were performed essentially as described in (Nyman et al., 1998; Saarinen et al., 1999) and analysed by MALDI-TOF MS. The enzymes and their specific control reactions with characterised oligosaccharides were: β-N-acetylglucosaminidase (*Streptococcus pneumoniae*, recombinant, *E. coli*; Calbiochem, USA) digested GlcNAcβ1-6Gal-R but not GalNAcβ1-4GlcNAcβ1-3/6Gal-R; β1,4-galactosidase (*Streptococcus pneumoniae*, recombinant, *E. coli*; Calbiochem, USA) digested Galβ1-4GlcNAc-R but not Galβ1-3GlcNAc-R; α-mannosidase (Jack bean; Glyko, UK) transformed a mixture of high-mannose N-glycans to the Man₁GlcNAc₂ N-glycan core trisaccharide. Control digestions were performed in parallel and analysed similarly to the analytical exoglycosidase reactions.

Synthesis of UDP-GalN-biotin. UDP-galactosamine (UDP-GalN) is formed from UDP-Glc and galactosamine-1-phosphate by the action of galactose-1-phosphate uridyltransferase (E.C. 2.7.7.12; Sigma, USA). A typical synthesis protocol is described below. The reaction mixture contains 10 mM galactosamine-1-phosphate, 20 mM UDP-Glc, 5 U/ml of galactose-1-phosphate uridyltransferase, 100 mM Na-HEPES pH 8.0, 5 mM MgCl₂, and 5 mM β-mercaptoethanol. The reaction vessel is incubated at room temperature under nitrogen atmosphere for 3 days, after which nucleotide sugars are isolated from the reaction mixture with a graphitised carbon column essentially as in (Mäki et al., 2002). The nucleotide sugar mixture, containing UDP-Glc and UDP-GalN, is incubated with a molar excess of sulfosuccinimidyl-6-(biotinamido)hexanoate (sulfo-NHS-LC-biotin; Pierce, USA) in 50 mM NH₄HCO₃ at room temperature for 2.5 hours. The product, UDP-GalN-biotin, uridine 5'-diphospho-N-(6-biotinamidohexanoyl)galactosamine, is purified by gel filtration and reversed phase HPLC.

Labeling of terminal GlcNAc residues in oligosaccharides and tissue sections with UDP-GalN-biotin. N-(6-biotinamidohexanoyl)galactosamine can be transferred from UDP-GalN-biotin to a terminal GlcNAc containing acceptor with a recombinant β1,4-galactosyltransferase similar to the enzyme described in (Ramakrishnan and Qasba, 2002). In a typical procedure, an oligosaccharide acceptor such as GlcNAcβ1-3Galβ1-4GlcNAcβ1-3Galβ1-4Glc, or deparaffinised formalin-fixed paraffin-embedded tissue sections, are incubated at +37° C. with a reaction mixture containing 10 mM UDP-GalN-biotin, 160 U/l enzyme, 100 mM Tris-HCl, and 20 mM MnCl₂. After washing, the biotin groups are visualised by standard methods in the art, using streptavidin or avidin coupled reagents, for example streptavidin-FITC.

Figure 7A:
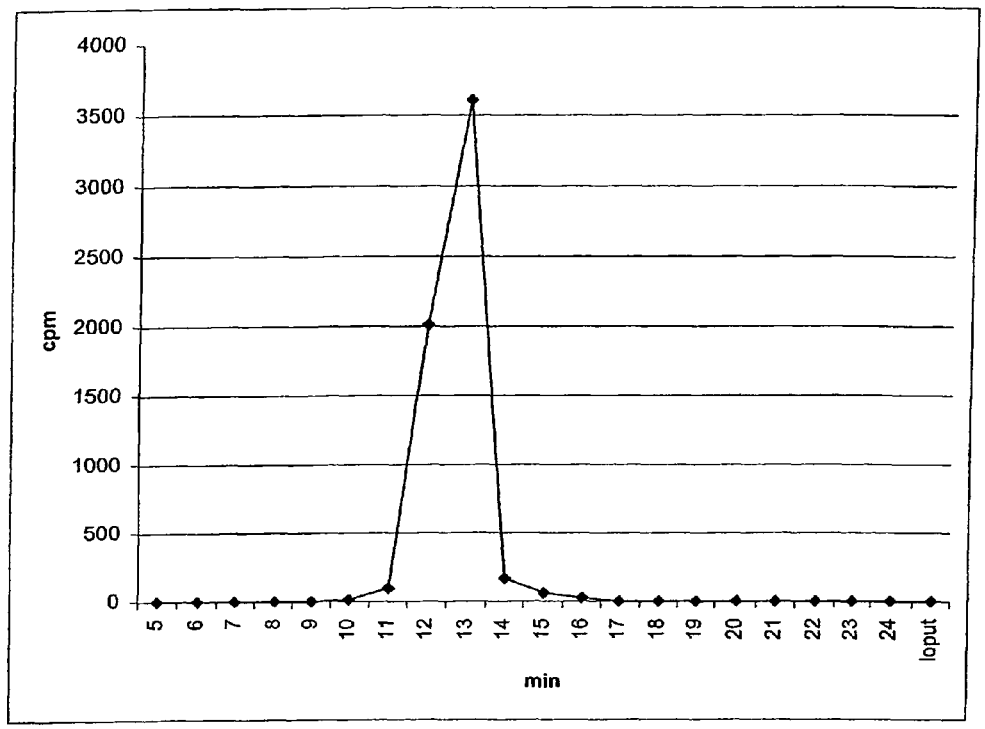
FIG. 7A. [$^{14}$C]Gal labelled oligosaccharides from N-glycosidase F digested lung adenocarcinoma sample. Glycans were subjected to gel filtration HPLC with a Superdex Peptide HR 10/30 column (Pharmacia, Sweden) in 50 mM NH$_4$HCO$_3$ (pH about 8.3) at a flow rate of 1 m/min. 1 ml fractions were collected and counted for radioactivity. Fractions at 12-15 min were pooled.
Figure 7B:
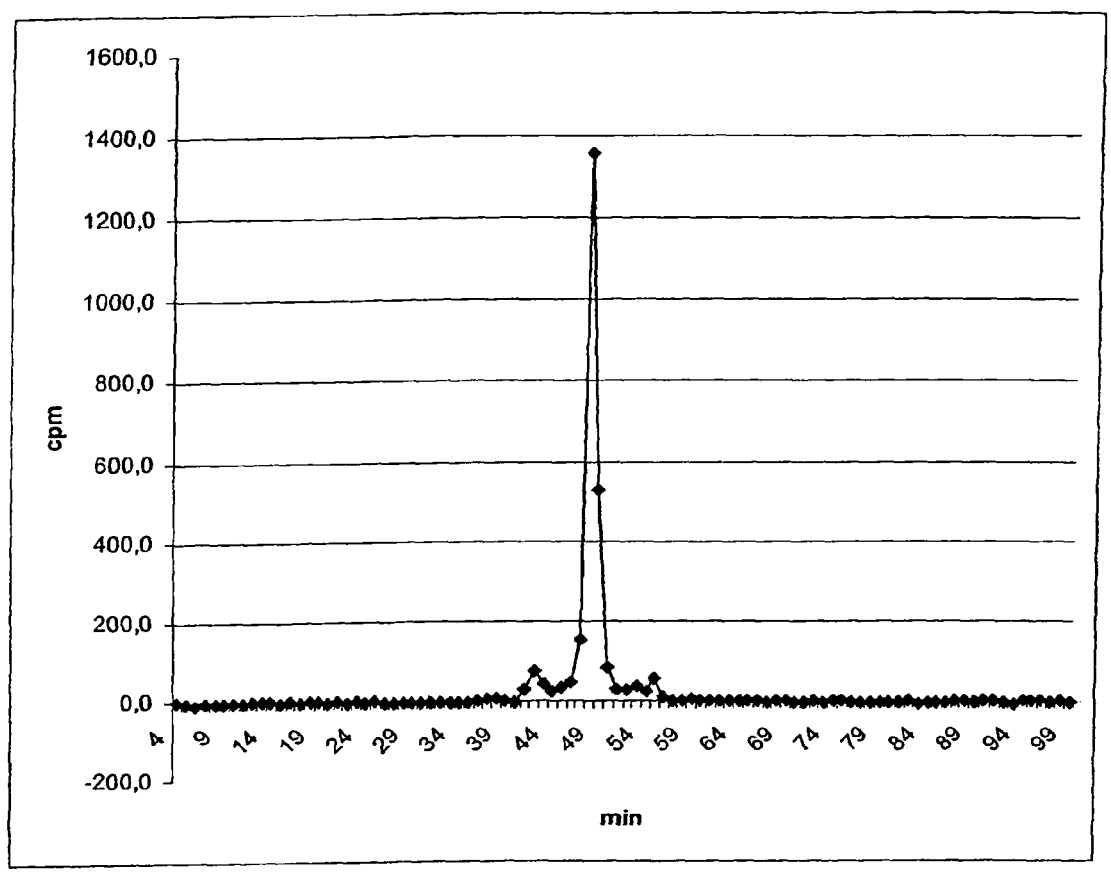
FIG. 7B. [$^{14}$C]Gal labelled oligosaccharides from N-glycosidase F digested lung adenocarcinoma sample. The 12-15 min pool from Superdex Peptide gel filtration HPLC (FIG. 10A) was subjected to HPLC with a 4.6×250 mm Hypercarb 5u column (Thermo Hypersil, USA) in 10 mM NH$_3$ at a flow rate of 0.7 ml/min, with a linear gradient of 0% to 40% acetonitrile in the mobile phase in 100 minutes. 0.7 ml fractions were collected and counted for radioactivity.

Labeling of terminal GlcNAc residues in tissue sections with UDP-[$^{14}$C]Gal. Formalin-fixed and paraffin-embedded tissue sections were deparaffinised and incubated at +37° C. with a reaction mixture containing UDP-[$^{14}$C]Gal, 200 U/l bovine milk β1,4-galactosyltransferase (Calbiochem, USA), 50 mM Na-MOPS pH 7.4, and 20 mM MnCl₂. After washing, the labelled sections were subjected to autoradiography. N-glycans were detached from the tissue sections with *Chryseobacterium meningosepticum* N-glycosidase F (Calbiochem, USA) essentially as in (Nyman et al., 1998). Chromatography was performed as described in figure legends to FIGS. 7A and 7B.

Example 5

Figure 3A:
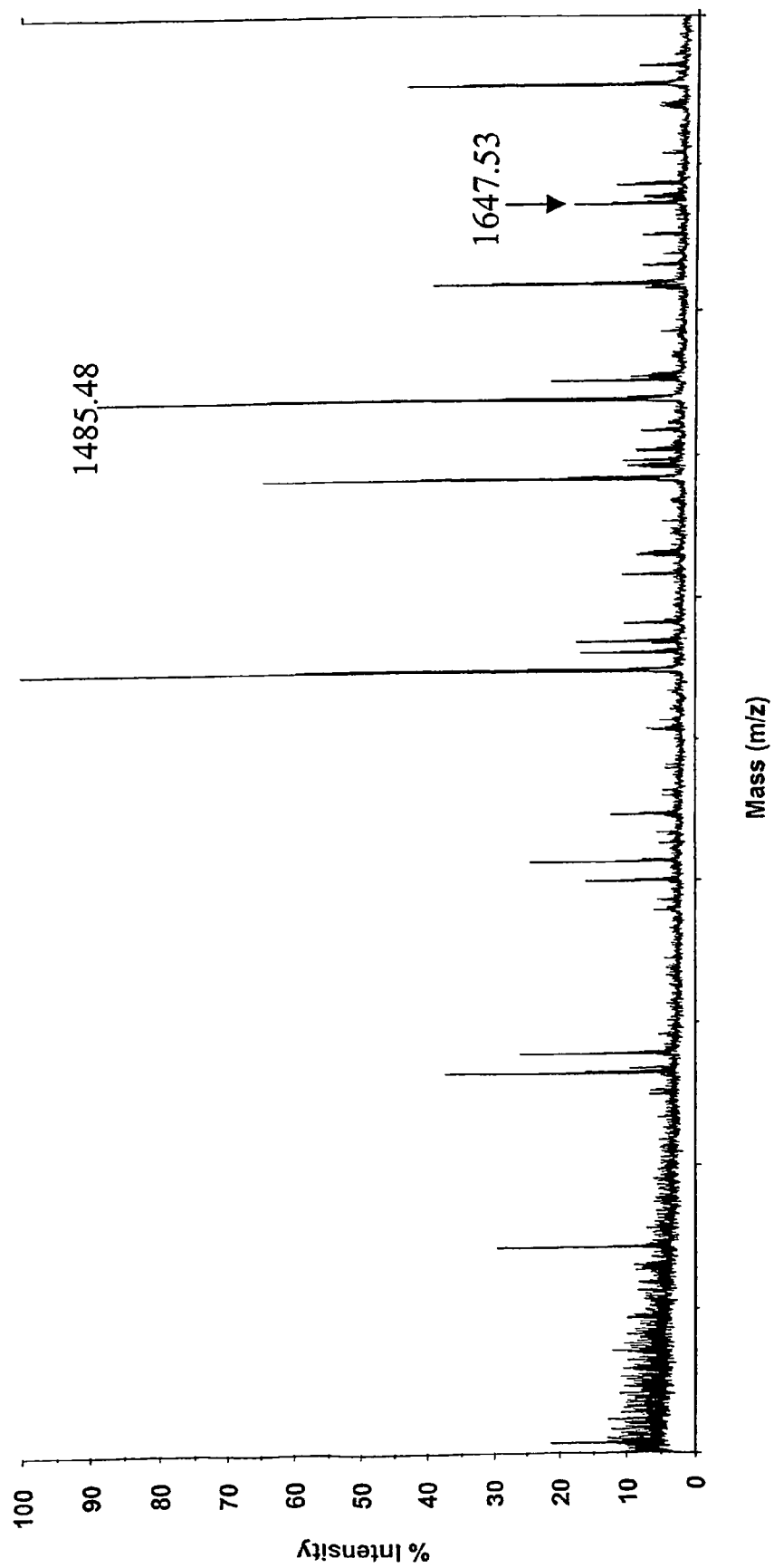
FIG. 3A. Positive ion reflector mode MALDI-TOF mass spectrum of lung adenocarcinoma sample neutral glycans.
Figure 3B:
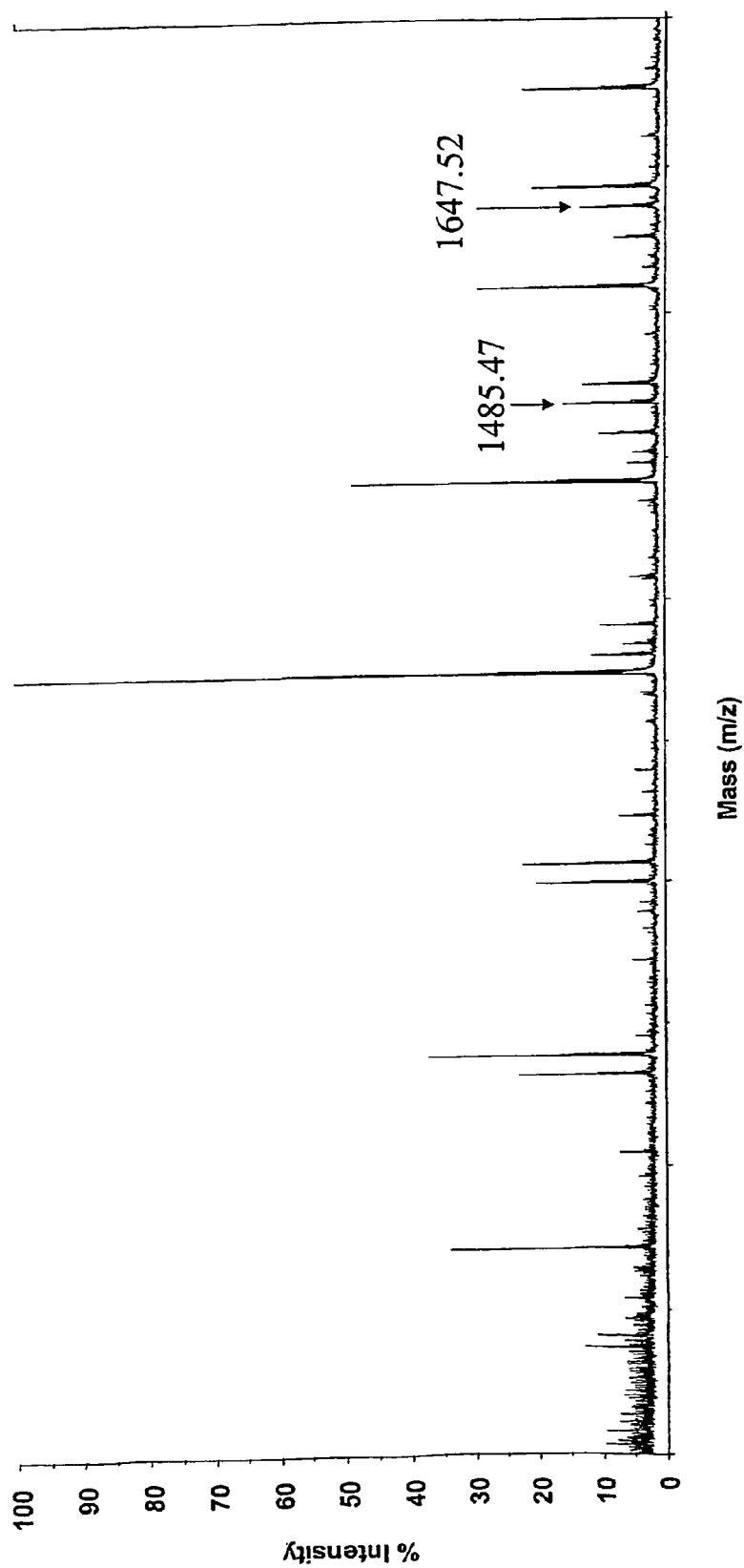
FIG. 3B. Positive ion reflector mode MALDI-TOF mass spectrum of healthy lung sample neutral glycans.
Figure 3C:
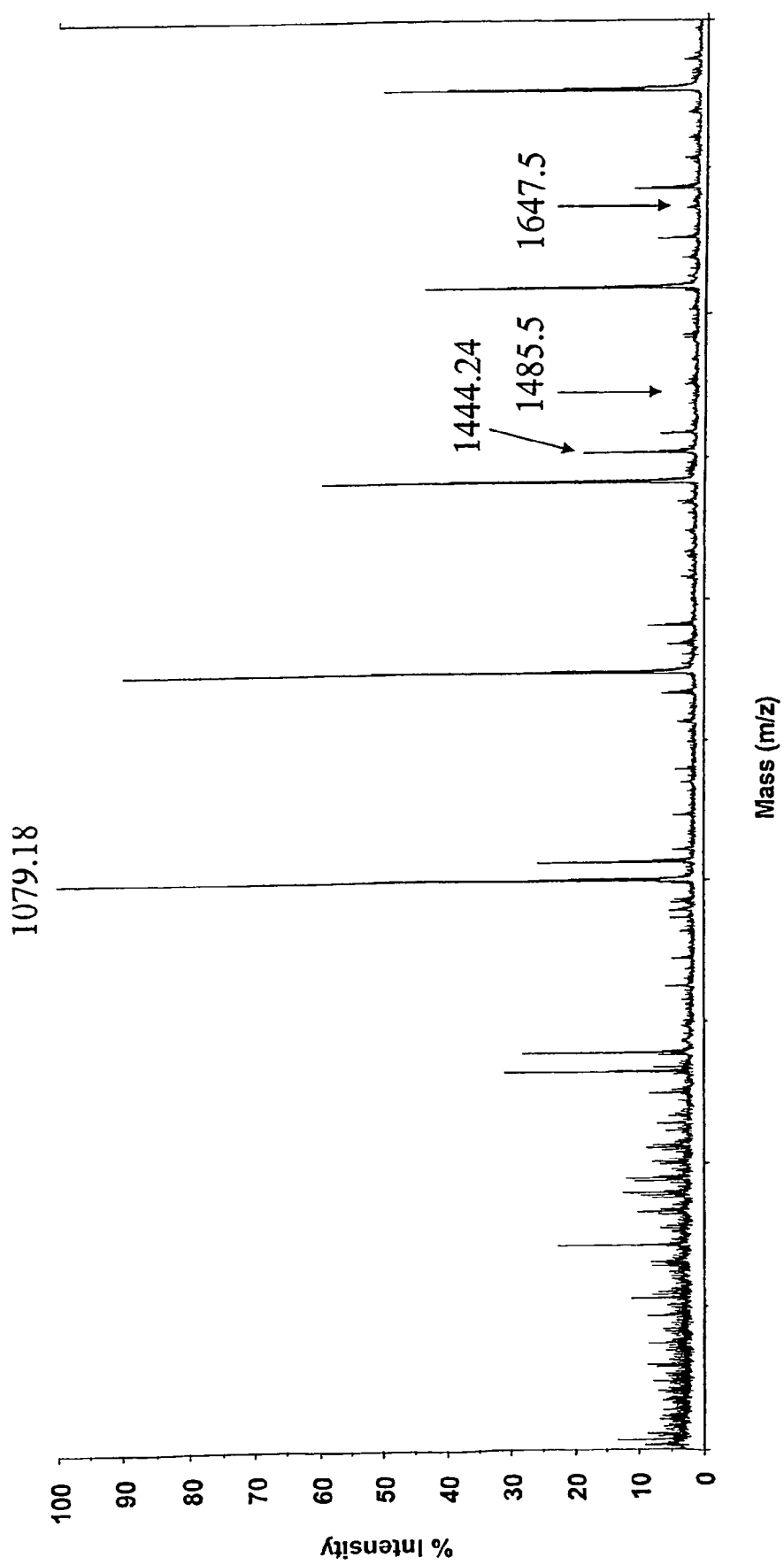
FIG. 3C. Positive ion reflector mode MALDI-TOF mass spectrum of lung adenocarcinoma sample neutral glycans after *S. pneumoniae* β-N-acetylglucosaminidase digestion.
Figure 3D:
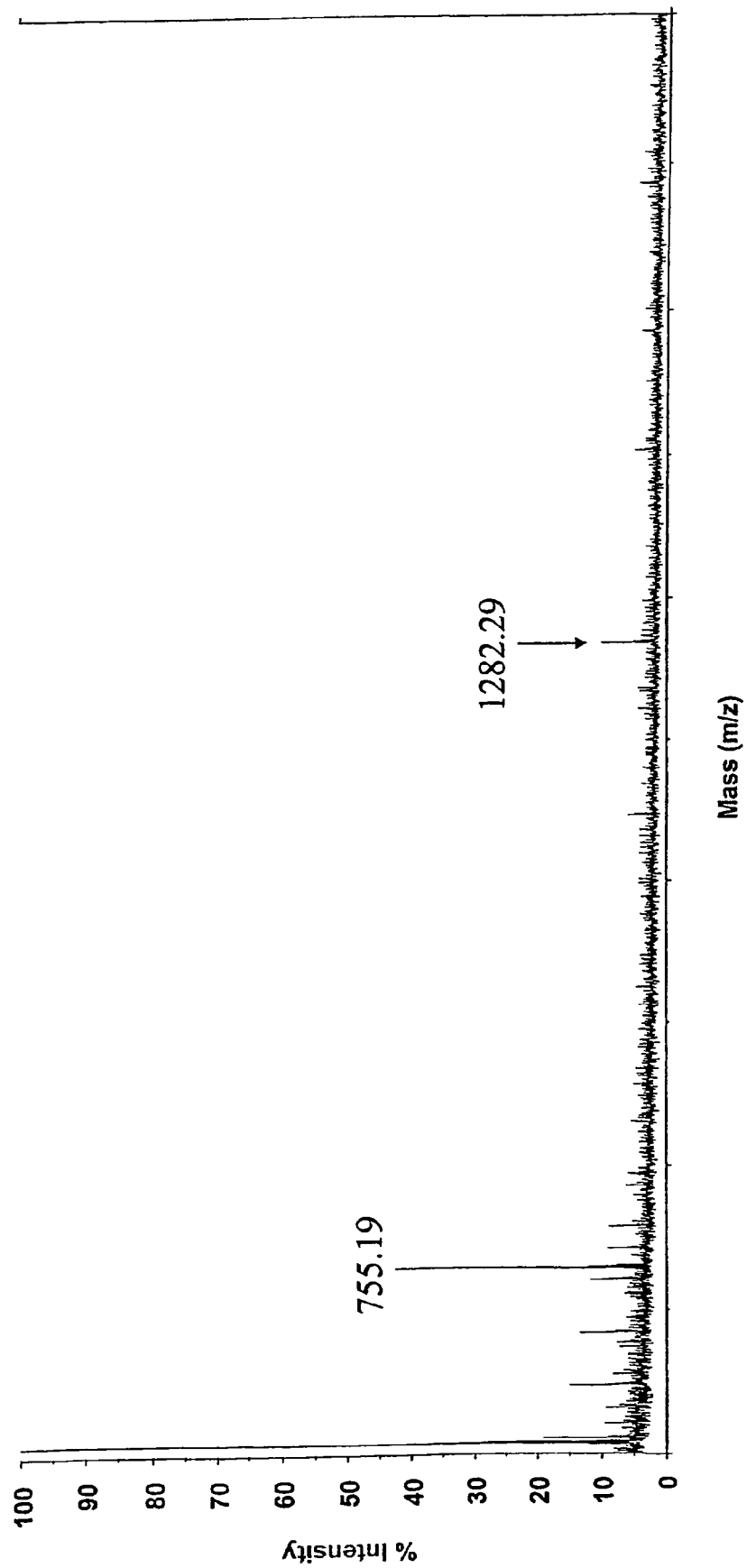
FIG. 3D. Positive ion reflector mode MALDI-TOF mass spectrum of lung adenocarcinoma neutral glycans after *S. pneumoniae* β-N-acetylglucosaminidase and jack bean α-mannosidase digestions.

Cancer-associated terminal GlcNAc containing N-glycans from lung adenocarinoma samples. Formalin-fixed samples, from tumor and surrounding healthy tissue, were obtained from a patient with lung adenocarcinoma. There was a significant difference between the neutral glycans isolated from the tumor sample (FIG. 3A) and the healthy tissue sample (FIG. 3B), namely a peak at m/z 1485.48, corresponding to the ion [$Hex_3HexNAc_4Fuc_1$+Na]$^+$ (calc. m/z 1485.53). The relative intensity of this glycan peak was elevated over 6.1 times in the tumor sample, as compared to healthy tissue. Furthermore, a peak at m/z 1647.53, corresponding to the ion [$Hex_4HexNAc_4Fuc_1$+Na]$^+$ (calc. m/z 1647.59), had a higher signal intensity in the tumor sample. Upon β-N-acetylglucosaminidase digestion (FIG. 3C), the two peaks were completely transformed into peaks at m/z 1079.18, corresponding to the ion [$Hex_3HexNAc_2Fuc_1$+Na]$^+$ (calc. m/Z 1079.38), and 1444.24, corresponding to the ion [$Hex_4HexNAc_3Fuc_1$+Na]$^+$ (calc. m/z 1444.51), respectively, indicating the presence of terminal β-GlcNAc residues. Jack bean α-mannosidase digestion (FIG. 3D) further transformed these peaks into peaks at m/z 755.19, corresponding to the ion [$Hex_1HexNAc_2Fuc_1$+Na]$^+$ (calc. m/z 755.27), and 1282.29, corresponding to the ion [$Hex_3HexNAc_3Fuc_1$+Na]$^+$ (calc. m/z 1282.45), respectively. However, α-mannosidase digestion before the β-N-acetylglucosaminidase digestion did not affect the two peaks, indicating that the α-Man residues were subterminal to the β-GlcNAc residues. In addition, β1,4-galactosidase digestion of the original neutral glycan sample completely transformed the peak at m/z 1647.5 into the peak at m/z 1485.5, indicating the presence of a terminal Galβ1-4GlcNAc unit. Taken together, the results suggest that the lung adenocarcinoma tumor sample contained highly elevated amounts of the complex N-linked glycan core structure GlcNAcβMana1-6(GlcNAcβ-Manα1-3)Manβ1-4GlcNAcβ1-4(Fucα1-6)GlcNAc, and slightly elevated amounts of the mono-β1,4-galactosylated (to GlcNAc) derivative of the former structure, as compared to the surrounding healthy tissue.

Example 6

Occurrence of the terminal GlcNAc containing N-glycans in carcinoma samples. The occurrence of the abovementioned structures in various tumor and healthy control samples was studied by isolating and analysing the neutral glycan fractions by MALDI-TOF MS and exoglycosidase digestions. The analysed tumor-control pairs were: 7 lung cancer sample pairs, and one pair each of colon, stomach, and larynx cancer samples. It turned out that in every case the relative abundance of the two terminal GlcNAc containing N-glycan at m/z 1485.5, was elevated in the cancerous sample. However, there were significant individual differences in the expression levels of this glycan epitope both in the healthy state and in cancer. Table 1 summarizes the differential expression of the m/z 1485.5 N-glycan in relation to the bulk of the isolated neutral glycan fraction.

Example 7

Figure 4A:
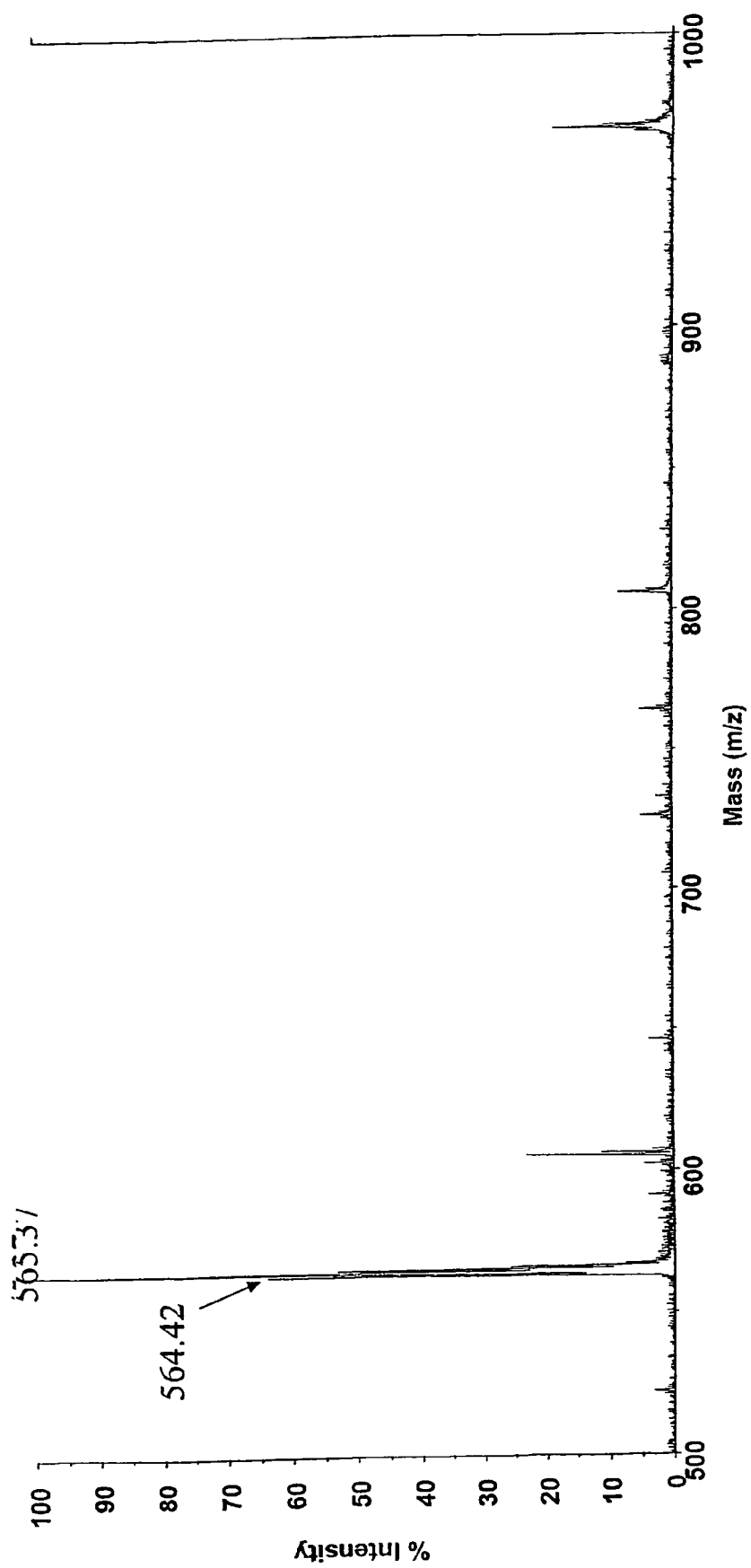
FIG. 4A. Negative ion linear mode MALDI-TOF mass spectrum of purified nucleotide sugars after UDP-galactosamine synthesis reaction.
Figure 4B:
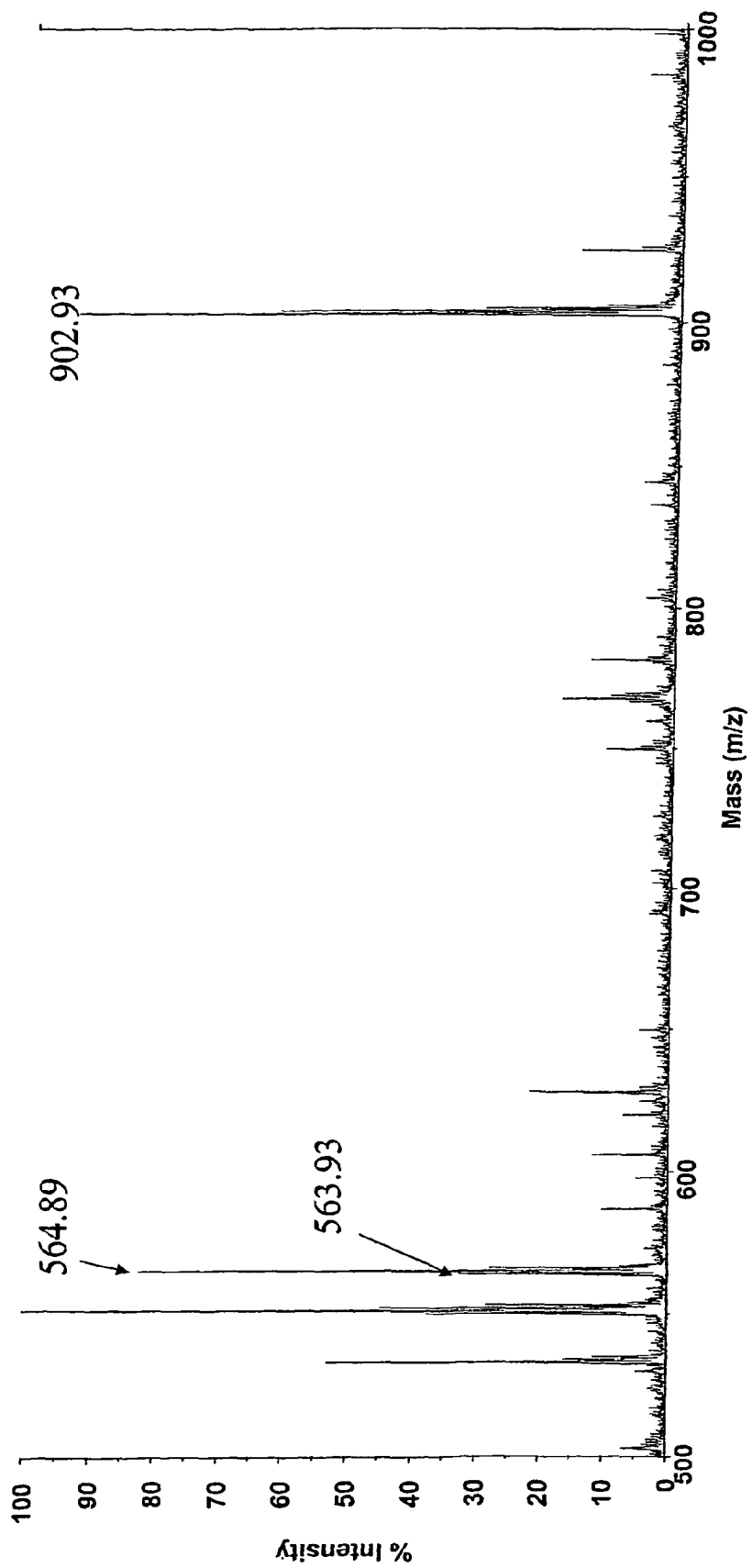
FIG. 4B. Negative ion linear mode MALDI-TOF mass spectrum of purified nucleotide sugars after the UDP-GalN-biotin synthesis reaction.
Figure 5:
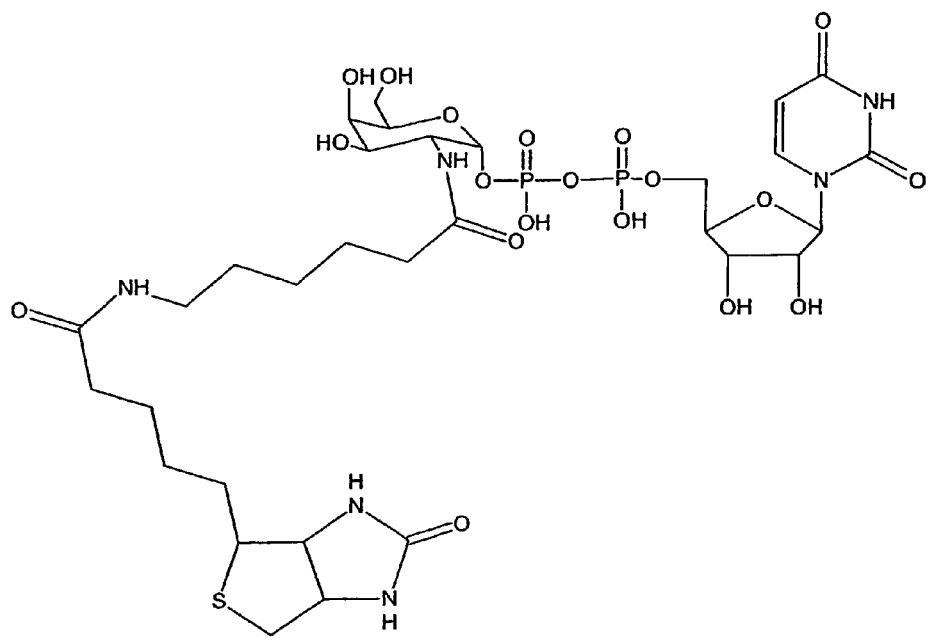
FIG. 5. Structure of UDP-GalN-biotin, uridine 5'-diphospho-N-(6-biotinamidohexanoyl)galactosamine.

Synthesis of UDP-GalN-biotin. UDP-galactosamine was synthesized as described under Materials and Methods. The product was characterized by MALDI-TOF MS (obs. m/z 564.42 for [$C_{15}H_{25}N_3O_{16}P_2$—H]$^-$, calc. m/z 564.31); FIG. 4A) and the expected peak appeared in the mass spectrum one mass unit smaller than the peak of UDP-Glc (obs. m/z 565.37 for [$C_{15}H_{24}N_2O_{17}P_2$—H]$^-$, calc. m/z 565.29); FIG. 4A). The crude nucleotide sugar preparate was reacted with a biotinylation reagent, namely succinimidyl-6-(biotinamido)hexanoate. After the reaction, the expected product could be seen in the MALDI-TOF mass spectrum of the reaction mixture (obs. m/z 902.93 for [$C_{31}H_{50}N_6O_{19}P_2S$—H]$^-$, calc. m/z 903.76; FIG. 4B). UDP-Glc did not react at all with the biotinylation reagent. The synthesized UDP-GalN-biotin, uridine 5'-diphospho-N-(6-biotinamidohexanoyl)galactosamine, reacted with GlcNAcβ1-3Galβ1-4GlcNAcβ1-3Galβ1-4Glc and a recombinant β1,4-galactosyltransferase similar to the enzyme described in (Ramakrishnan and Qasba, 2002). The product, [N-(6-biotinamidohexanoyl)galactosamine]β1-4GlcNAcβ1-3Galβ1-4GlcNAcβ1-3Galβ1-4Glc, was characterized by MALDI-TOF MS (obs. m/z for [M+Na]$^+$ 1433.38, calc. m/z 1433.55). Taken together, the results indicate that the synthesized product has the expected structure (FIG. 5). The product was chromatographically purified to homogeneity.

Example 8

Figure 6:
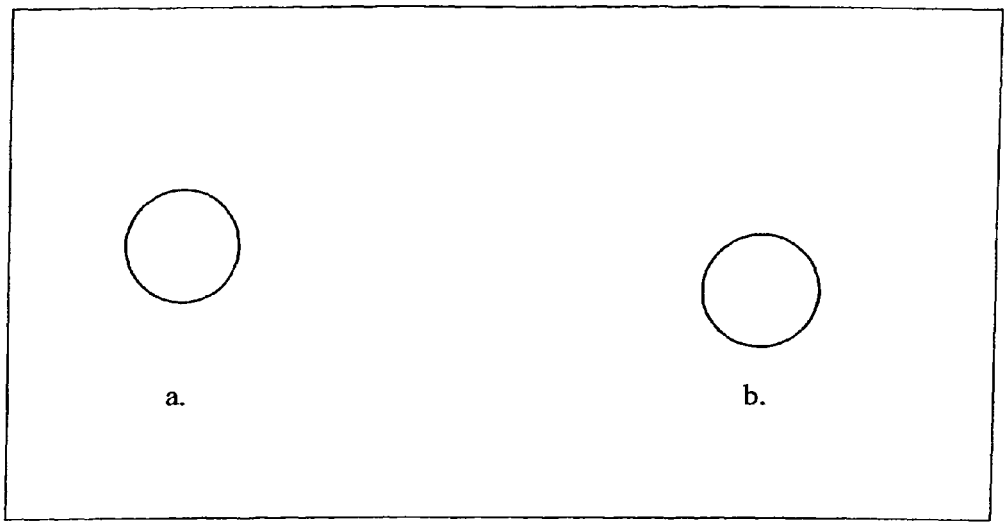
FIG. 6. Autoradiography of [$^{14}$C]Gal labelled lung adenocarcinoma (a.) and healthy lung tissue (b.) sections.

Labeling of terminal GlcNAc residues in tissue sections with UDP-[$^{14}C$]Gal and UDP-GalN-biotin. Deparaffinised formalin-fixed and paraffin-embedded tissue sections were radioactively labeled with UDP-[$^{14}C$]Gal and bovine milk β1,4-galactosyltransferase, as described under Materials and Methods. Autoradiography revealed a clear difference between the tumor and the healthy tissue samples (FIG. 6), indicating that there are highly elevated amounts of terminal GlcNAc residues in the lung adenocarcinoma sample. Similar results were also obtained by using the UDP-GalN-biotin reagent, as described under Materials and Methods, streptavin-FITC, and fluorescence microscopy. Importantly, cancer cells could be labeled with this biotinylation reagent.

Example 9

Isolation of [$^{14}C$] Gal-labeled oligosaccharides from lung adenocarcinoma sample. After labeling of lung adenocarcinoma sample and surrounding healthy tissue sections with [$^{14}C$]Gal as described above, the labeled oligosaccharides were isolated by N-glycosidase F digestion and nonreductive β-elimination. In the gel filtration chromatogram of the N-glycosidase F liberated glycans from lung adenocarcinoma (FIG. 7A), only one peak was visible and it coeluted with the N-glycan standards Galβ1-4GlcNAcβ1-2Manα1-6(Galβ1-4GlcNAcβ1-2Manα1-3)Manβ1-4GlcNAcβ1-4(Fucα1-6) GlcNAc and Galβ1-4[GlcNAcβ1-2Manα1-6(GlcNAcβ,1-2Manα1-3)Manβ1-4GlcNAcβ1-4(Fucα1-6)GlcNAc]. The peak was pooled and subjected to HPLC with a porous graphitized carbon column (FIG. 7B), where it was divided into one major and two minor peaks. The major peak, containing nearly all of the total radioactivity, coeluted with the N-glycan standard Galβ1-4[GlcNAcβ1-2Manα1-6 (GlcNAcβ1-2Manα1-3)Manβ1-4GlcNAcβ1-4(Fucα1-6) GlcNAc].

Figure 7C:
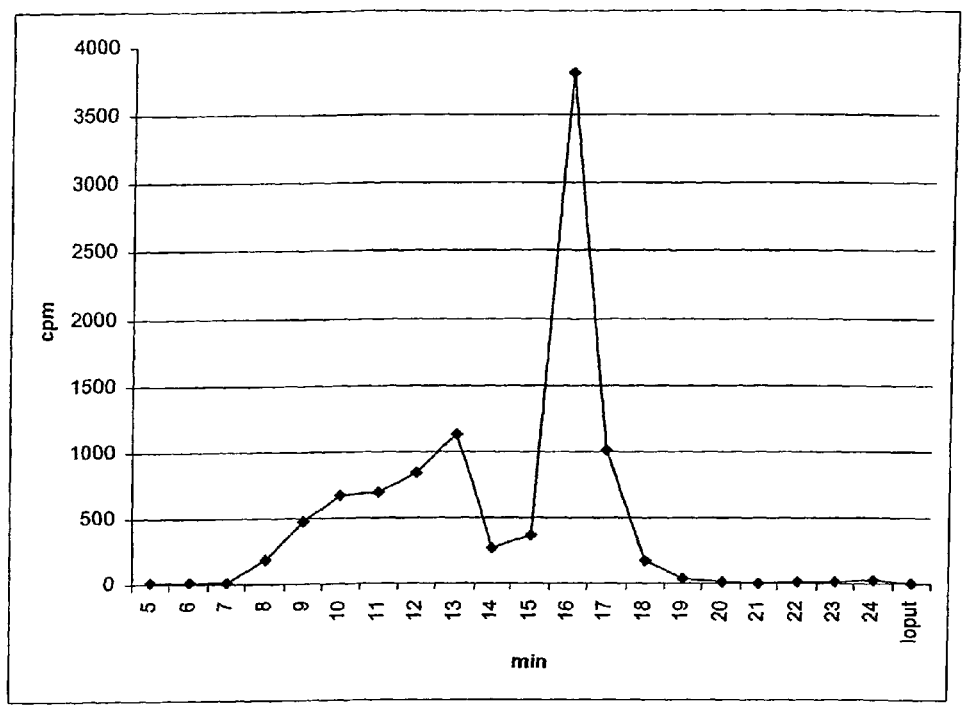
FIG. 7C. [$^{14}$C]Gal labelled material released by nonreductive β-elimination from lung adenocarcinoma sample. The material was subjected to gel filtration HPLC with a Superdex Peptide HR 10/30 column (Pharmacia, Sweden) in 50 mM NH$_4$HCO$_3$ at a flow rate of 1 ml/min. 1 ml fractions were collected and counted for radioactivity. Fractions at 8-15 min (pool 1) were pooled as well as at 15-18 min (pool 2).

In the gel filtration HPLC chromatogram of the material liberated by nonreductive β-elimination from lung adenocarcinoma (FIG. 7C), a broad peak, containing 45% of the total radioactivity, was found to elute between the void volume (at 8 ml) and the elution position of the N-glycan standard Galβ14[GlcNAcβ1-2Manα1-6(GlcNAcβ1-2Manα1-3)

Manβ1-4GlcNAcβ1-4(Fucα1-6)GlcNAc]. The broad peak was pooled and passed through columns of strong cation exchange material and $C_{18}$ silica, which would retain all glycopeptidic material, but allow for quantitative elution of free oligosaccharides. Nearly 80% of the radioactivity in the pooled fractions was retained in the columns, indicating that the broad peak indeed corresponded to alkali-liberated glycopeptides, from which the [$^{14}$C]Gal labeled glycan moieties had not been detached. Major part of the remaining radioactivity was found to correspond to the N-glycan structure described above, but the presence of other labelled oligosaccharides could not be excluded. The major peak in the gel filtration HPLC chromatogram, containing 55% of the total radioactivity, coeluted with an N-acetyllactosamine (LacNAc) standard.

Example 10

Protein linked GlcNAc from cancer samples. Furthermore, in graphitized carbon column HPLC of the pooled fractions at 15-18 min, the major peak coeluted with LacNAc. This suggests that the sample contains base-labile GlcNAc monosaccharide-protein conjugates, most likely GlcNAcβ-O-Ser/Thr units. Importantly, the amount of [$^{14}$C]-labeled LacNAc was significantly (1.99 times) higher in the lung adenocarcinoma sample as compared to the surrounding healthy tissue sample.

Taken together, these results indicate that about half of the total radioactivity that can be liberated from UDP-[$^{14}$C]Gal labeled lung adenocarcinoma sample tissue sections, represents the [$^{14}$C]Gal labeled forms of the cancer-associated N-glycan GlcNAcβ-Manα1-6(GlcNAcβ-Manα1-3)Manβ1-4GlcNAcβ1-4(Fucα1-6)GlcNAc. Furthermore, it is evident that also in the UDP-GalN-biotin reaction, the label is transferred into the oligosaccharide structures characterized above.

Example 11

Figure 8:
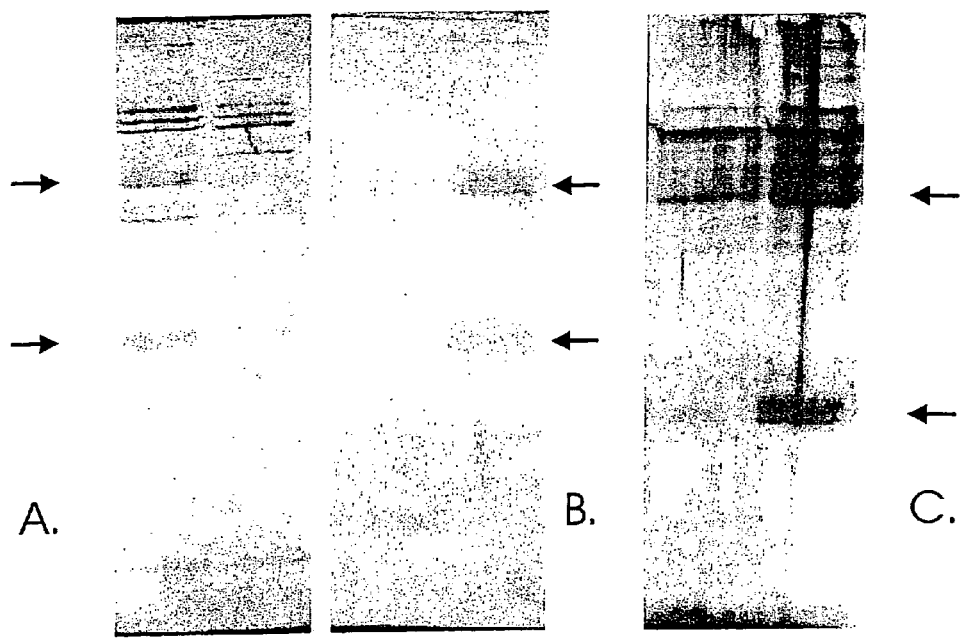
FIG. 8. Coomassie Blue stained reducing SDS-PAGE gels. Arrowheads indicate the position IgG heavy and light chains, respectively. (A.) Serum from a person who had recovered from mucinous ovarian adenocarcinoma, GlcNAcβ1-6(Galβ1-3)GalNAcα Sepharose; left: 0.5 M GlcNAc elution, right: acidic elution. (B.) IgG from pooled human sera, GlcNAcβ1-6(Galβ1-3)GalNAcα Sepharose; left: 0.5 M GlcNAc elution, right: acidic elution. (C.) Silver stained gel Serum from a person who had recovered from mucinous ovarian adenocarcinoma, Galβ1-4GlcNAcβ1-6(Galβ1-3)GalNAcα Sepharose; left: 0.5 M GlcNAc elution, right: acidic elution.

Isolation of anti-GlcNAc antibodies from human serum. Human serum from a person who had recovered from mucinous ovarian adenocarcinoma, was passed through Sepharose columns that contained either GlcNAcβ1-6(Galβ1-3)GalNAcα or Galβ1-4GlcNAcβ1-6(Galβ1-3)GalNAcαepitopes covalently coupled to the gel. After washing, the columns were firstly eluted with a buffer containing 0.5 M GlcNAc (specific elution), and secondly with acidic buffer (unspecific elution). As a control, an IgG preparation from pooled human sera from healthy donors, i.e. persons who did not have a history of malignant diseases, was also subjected to the abovementioned chromatographical procedure. Reducing SDS-PAGE analysis was done to the collected fractions (FIG. 8). From the results it can be seen that two bands corresponding to proteins that had similar relative molecular weights to the heavy and light chains of an IgG standard, were eluted in the specific 0.5 M GlcNAc elution of GlcNAcβ1-6(Galβ1-3)GalNAcα Sepharose, but only in the serum sample of the person who had recovered from cancer. In contrast, no such specific elution could be detected in Galβ1-4GlcNAcβ1-6(Galβ1-3)GalNAcα Sepharose chromatography of the two samples. According to their relative molecular weight, the specifically eluted proteins are likely to represent the heavy and light chain subunits of IgG or IgA, but not IgM human antibodies. The present results indicate the presence of elevated levels of terminal GlcNAc specific antibodies in serum of the person who had recovered from cancer, more specifically IgG and/or IgA antibodies that recognize the GlcNAcβ1-6(Galβ1-3)GalNAcα glycan epitope.

TABLE 1

Relative abundances, against the most abundant N-glycans in the sample, of the terminal GlcNAc residues containing N-glycan peak at m/z 1485.5, of several tumor and healthy tissue control samples.

| patient (sample) | relative abundance of the peak at m/z 1485.5: | |
|---|---|---|
| | tumor sample | healthy tissue |
| lung cancer | | |
| A | 86 | 13 |
| B (1) | 109 | 67 |
| B (2) | 101 | |
| C (1) | 35 | 18 |
| C (2) | 22 | |
| D (1) | 18 | 10 |
| D (2) | 14 | |
| E | 62 | 42 |
| F | 32 | 27 |
| G | 23 | 12 |
| colon cancer | | |
| H | 32 | 0 |
| stomach cancer | | |
| I | 41 | 38 |
| larynx cancer | | |
| J | 67 | 15 |

REFERENCES

Arap, W., Pasqualini, R. and Ruoslahti, E. (1998) Science 279, 323-4.

Ernst, B., Hart, G. W., and Sinaÿ, P. (eds.) (2000) Carbohydrates in chemistry and biology, ISBN 3-527-29511-9, Weiley-VHC, Weinheim.

Hanisch, F.-G., Koldovsky, U., and Borchard F. (1993) Cancer Res. 53, 4791-4796.

Hansson, G. C., Karlsson, K.-A., Larson G., Strömberg, N., and Thurin, J. (1985) Anal. Biochem. 146, 158-63.

Harvey, D. J., et al. (1993) Rapid Commun. Mass Spectrom. 7(7):614-9.

Hounsell, E. F., Lawson, A. M., Stoll, M., Kane, D. P., Cashmore, G. C., Carruthers, R. A., Feeney, J., and Feizi, T. (1989) Eur. J. Biochem. 186, 597-610.

Holmes, E. H., and Greene, T. G. (1991) Arch. Biochem. Biophys. 288, 87-96.

Hu, J., Stults, C. L. M., Holmes, E. H., and Macher, B. A. (1994) Glycobiology 4, 251-257.

Nakamura, M., Tsunoda, A., Sakoe, K, and Saito, M. (1993) Biochem. Biophys. Res. Commun. 197 1025-1033.

Manzi, A. E., et al. (2000) Glycobiology 10(7):669-89.

Mäki, M., et al. (2002) Eur. J. Biochem. 269(2):593-601.

Nyman, T. A., et al. (1998) Eur. J. Biochem. 253(2):485-93.

Packer, N. H., et al. (1998) Glycoconj. J. 15(8):737-747.

Ramakrishnan, B., and Qasba, P. K. (2002) J. Biol. Chem. 277(23):20833-9.

Papac, D. I., et al. (1996) Anal. Chem. 68(18):3215-23.

Rhen M., Klemm P., and Korhonen T. K. (1986). J Bacteriol 168, 1234-42.

Symington, F. W, Hendersson, B. A., and Hakomori, S.-I. (1984) Mol. Immunol. 21, 877-882.

Saarinen, J., et al. (1999) Eur. J. Biochem. 259(3):829-40.

Teneberg, S., Lönnroth, I., Torres López, J. T., Galili, U., Ölwegård Halvarsson, M., Ångström, J., and Karl-Anders Karlsson (1996) Glycobiology 6, 599-609.

Verostek, M. F., et al. (2000) Anal. Biochem. 278:111-122.

Teneberg S, Ångström J, Jovall P-Å, and Karlsson K-A. (1994) J Biol Chem 269, 8554-63.

What is claimed:

1. A method for diagnosing cancer or tumor in a biological sample suspected to contain tumor tissue, wherein said sample is taken from the lung, ovary, colon, kidney, larynx or stomach of a human patient, the method comprising determining in said sample the presence of an oligosaccharide sequence having a terminal GlcNAcβ3/6Gal structure and comparing the level of presence of said oligosaccharide sequence in said sample to the level of presence of said oligosaccharide sequence in comparable normal tissue, wherein an increase in the amount of said oligosaccharide sequence in said sample as compared to the amount found in comparable normal tissue is indicative of the presence of tumor or cancer in said sample.

2. A method for diagnosing tumor in a biological sample suspected to contain tumor tissue, wherein said sample is taken from a human patient, the method comprising determining in said sample the presence of an oligosaccharide sequence having terminal GlcNAcβ3/6Gal structure and comparing the level of presence of said oligosaccharide sequence in said sample to the level of presence of said oligosaccharide sequence in comparable normal tissue, wherein an increase in the amount of said oligosaccharide sequence in said sample as compared to the amount found in comparable normal tissue is indicative of the presence of tumor in said sample.

3. The method according to claim 1, wherein the determination comprises
   (a) contacting said biological sample with a substance binding to said oligosaccharide sequence to form a combination of said substance bound to said oligosaccharide, and
   determining the amount of said a combination of said substance and said sample, wherein an increase in the amount of said combination in said sample as compared to the amount found in comparable normal cells is an indication of cancer being present in said sample, or
   (b) releasing the oligosaccharide structures of said biological sample by enzymatic or chemical methods to form a fraction containing free oligosaccharide structures from said sample, and
   determining the amount of said oligosaccharide sequence in said fraction, wherein an increase in the amount of said oligosaccharide sequence in said fraction as compared to the amount found in comparable normal cells is an indication of cancer being present in said sample.

4. The method according to claim 2, wherein the determination comprises
   (a) contacting said biological sample with a substance binding to said oligosaccharide sequence to form a combination of said substance bound to said oligosaccharide, and
   determining the amount of a combination of said substance and said sample, wherein an increase in the amount of said combination as compared to the amount found in comparable normal cells is an indication of tumor being present in said sample, or
   (b) releasing the oligosaccharide structures of said biological sample by enzymatic or chemical methods to form a fraction containing free oligosaccharide structures from said sample, and
   determining the amount of said oligosaccharide sequence in said fraction, wherein an increase in the amount of said oligosaccharide sequence in said fraction as compared to the amount found in comparable normal cells is an indication of tumor being present in said sample.

5. The method according to claim 3 or 4, wherein a cancer or tumor type is determined.

6. The method according to claim 3 or 4, wherein the glycosylations are determined on the surface of cancer and normal tissue.

7. The method according to claim 3 or 4, wherein the substance binds to at least one of the human tumor specific terminal GlcNAcβ3/6Gal oligosaccharide sequences selected from the group consisting of
   GlcNAcβ3Gal, GlcNAcβ3Galβ4Glc,
   GlcNAcβ3Galβ4GlcNAc,
   GlcNAcβ3Galβ4GlcNAcβ3Gal,
   GlcNAcβ3Galβ4GlcNAcβ3Galβ4Glc, GlcNAcβ6Gal,
   and GlcNAcβ6Galβ4GlcNAc.

8. The method according to claim 3, wherein the substance is a human antibody and wherein said human cancer is hypernephroma, cancer of larynx, colon cancer, or lung cancer.

9. The method according to claim 4, wherein the substance is a human antibody and the oligosaccharide sequence is selected from the group consisting of GlcNAcβ3Gal, GlcNAcβ3Galβ4Glc, GlcNAcβ3Galβ4GlcNAcβ3Gal, GlcNAcβ3Galβ4GlcNAcβ3Galβ4Glc, GlcNAcβ6Gal, and GlcNAcβ6Galβ4GlcNAc.

10. The method according to claim 1 or 2, wherein said human tumor is hypernephroma, cancer of larynx, colon cancer, or lung cancer.

11. The method according to claim 1 or 2, wherein the tumor specific oligosaccharide sequence is GlcNAcβ3Galβ4GlcNAcβ3Gal or GlcNAcβ3Galβ4GlcNAcβ3Galβ4Glc.

12. The method according to claim 1 or 2, wherein the sample to be diagnosed is taken from a patient being under immunosuppressive medication or suffering from immunodeficiency.

13. The method according to claim 1 or 2, wherein said human tumor is a human solid tumor.

14. The method according to claim 3 or 4, wherein said substance binding to said oligosaccharide sequence is an aptamer, a peptide or a protein.

15. The method according to claim 14, wherein said protein is an antibody, a lectin, or a fragment thereof.

16. The method according to claim 15, wherein said protein is an enzyme recognizing the terminal GlcNAc-structures, preferably a glycosyltransferase enzyme or variant thereof.

17. The method according to claim 15, wherein said antibody is a human or humanized antibody.

18. The method according to claim 1, wherein said human terminal GlcNAcβ3/β6 oligosaccharide sequence is selected from the group of O-glycan type structures consisting of
GlcNAcβ3Galβ3(Galβ4GlcNAcβ6)GalNAc,
lcNAcβ3Galβ3(GlcNAcβ6)GalNAc,
GlcNAcβ3Galβ3GalNAc, Galβ3(GlcNAcβ6)GalNAc, and GlcNAcβ6GalNAc.

19. The method according to claim 10, where said tumor is lung cancer.

20. The method according to claim 10, wherein the tumor is in lung, ovary, colon, or kidney and the oligosaccharide is GlcNAcβ3Galβ4GlcNAcβ3Galβ4Glc or GlcNAcβ3Galβ4Glc.

21. The method according to claim 10, wherein the tumor is in ovary or kidney and the oligosaccharide is GlcNAcβ6(GlcNAcβ3)Galβ4GlcNAc or GlcNAcβ6Galβ4GlcNAc.

* * * * *